US 7,926,856 B2

(12) United States Patent
Smutney et al.

(10) Patent No.: US 7,926,856 B2
(45) Date of Patent: Apr. 19, 2011

(54) FLUID CONDUIT CONNECTION

(75) Inventors: Chad C. Smutney, Wethersfield, CT (US); P. Spencer Kinsey, Danbury, CT (US); John M. Polidoro, Coventry, CT (US); Petter Hedstrom, Haverhill, MA (US); Gregory Melville, Hudson, NH (US); Timothy J. Morrill, Plaistow, NH (US); Richard D. Nelson, Woburn, MA (US)

(73) Assignee: Smith & Nephew, Inc., Memphis, TN (US)

( * ) Notice: Subject to any disclaimer, the term of this patent is extended or adjusted under 35 U.S.C. 154(b) by 60 days.

(21) Appl. No.: 11/681,680

(22) Filed: Mar. 2, 2007

(65) Prior Publication Data

US 2008/0214990 A1 Sep. 4, 2008

(51) Int. Cl.
*F16L 25/00* (2006.01)
*F16L 35/00* (2006.01)
*A61M 25/16* (2006.01)

(52) U.S. Cl. ...................................... 285/330; 604/535

(58) Field of Classification Search ............ 604/27, 604/533, 534, 535, 537, 538, 164.01, 164.07, 604/164.08, 170.02, 161; 285/305, 314, 285/317, 319, 330
See application file for complete search history.

(56) References Cited

U.S. PATENT DOCUMENTS

| 4,506,862 A | * | 3/1985 | Spinosa et al. ............. 251/149.5 |
| 5,251,873 A | | 10/1993 | Atkinson et al. |
| 5,976,115 A | * | 11/1999 | Parris et al. ................... 604/533 |
| 6,146,374 A | | 11/2000 | Erskine et al. |
| 6,152,913 A | | 11/2000 | Feith et al. |
| 6,155,607 A | | 12/2000 | Hewitt et al. |
| 6,158,458 A | | 12/2000 | Ryan |
| 6,260,890 B1 | * | 7/2001 | Mason ......................... 285/332 |
| 6,261,282 B1 | | 7/2001 | Jepson et al. |
| 6,267,754 B1 | | 7/2001 | Peters |
| 6,290,206 B1 | | 9/2001 | Doyle |
| 6,344,033 B1 | | 2/2002 | Jepson et al. |
| 6,364,869 B1 | | 4/2002 | Bonaldo |
| 6,390,120 B1 | | 5/2002 | Guala |
| 6,390,130 B1 | | 5/2002 | Guala |
| 6,394,983 B1 | | 5/2002 | Mayoral et al. |

(Continued)

OTHER PUBLICATIONS

"EMS Products"; http://www.progressivemed.com/emsproducts/iv/interlinksets.html, Dec. 2006, 3 pages.

*Primary Examiner* — Kevin C. Sirmons
*Assistant Examiner* — Bradley J Osinski
(74) *Attorney, Agent, or Firm* — Fish & Richardson P.C.

(57) ABSTRACT

A fluid conduit connector assembly includes a connector having a body with an inner surface defining a fluid channel. The connector also includes an inlet region for flow of fluid into the fluid channel, and an outlet region for flow of fluid from the fluid channel. The connector further includes an axial alignment member outward of the body, and a pair of flexible tabs arranged generally circumferentially of the alignment member and outward of the body. The connector can be configured as a day-side connector, transfer member with check valve, and/or patient-side connector. An implementation includes a day-side connector, a patient-side connector, and a transfer member, each of which has a pair of flexible tabs. The pairs of tabs are configured such that the transfer member releasably couples the day-side and patient-side connectors. A method for aseptically connecting a fluid conduit is also disclosed.

25 Claims, 24 Drawing Sheets

U.S. PATENT DOCUMENTS

| | | |
|---|---|---|
| 6,453,956 B2 | 9/2002 | Safabash |
| 6,482,188 B1 | 11/2002 | Rogers et al. |
| 6,537,263 B1 | 3/2003 | Aneas |
| 6,541,802 B2 | 4/2003 | Doyle |
| 6,595,964 B2 | 7/2003 | Finley et al. |
| 6,651,956 B2 | 11/2003 | Miller |
| 6,695,817 B1 | 2/2004 | Fangrow, Jr. |
| 6,722,705 B2 | 4/2004 | Korkor |
| 6,745,998 B2 | 6/2004 | Doyle |
| 6,808,161 B1 | 10/2004 | Hishikawa |
| 6,971,684 B2 * | 12/2005 | Ferrari ................ 285/319 |
| 7,401,818 B2 * | 7/2008 | Takayanagi ............ 285/319 |
| 2005/0082828 A1 * | 4/2005 | Wicks et al. ............ 285/319 |
| 2006/0142735 A1 * | 6/2006 | Whitley ................ 604/537 |

* cited by examiner

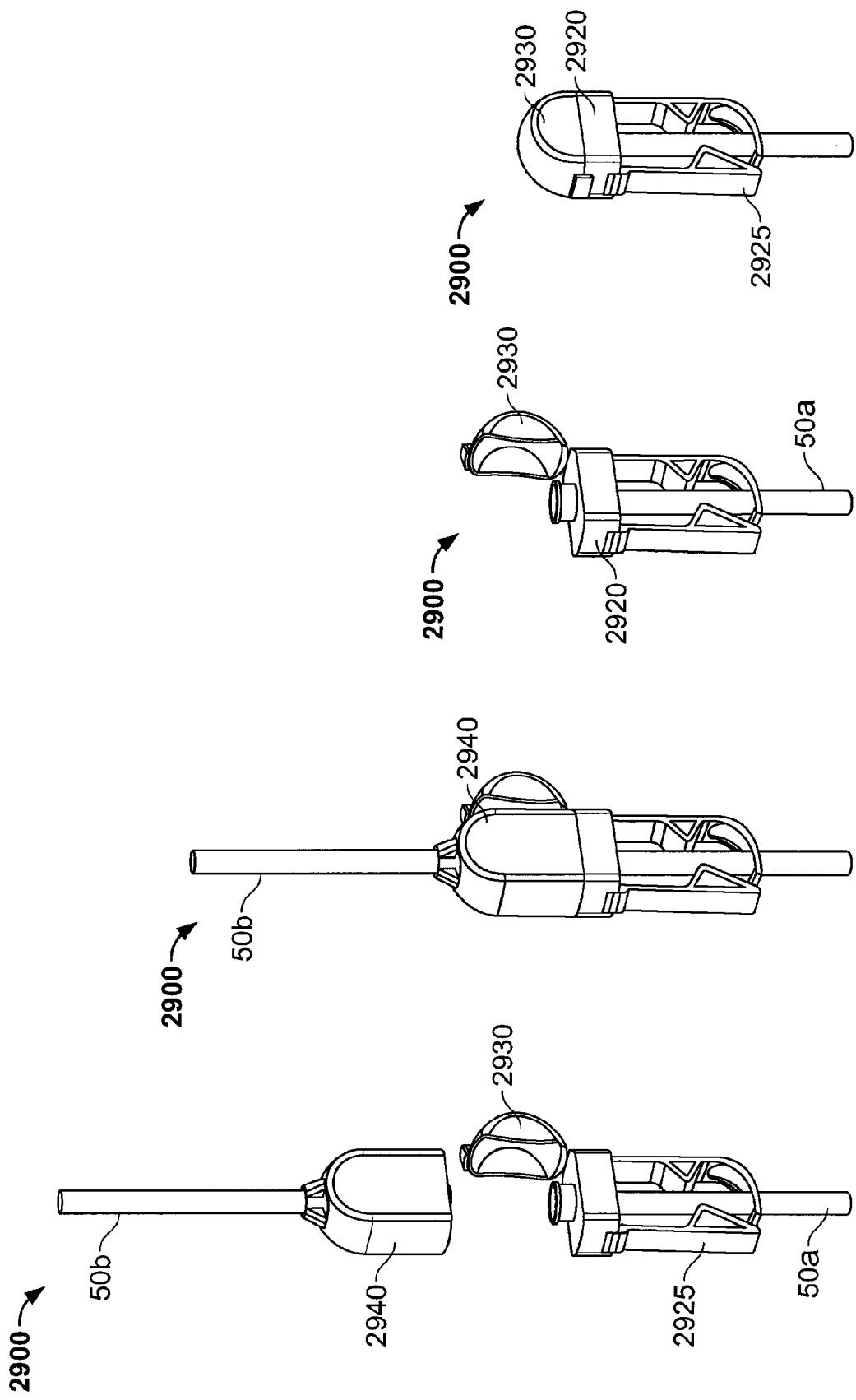

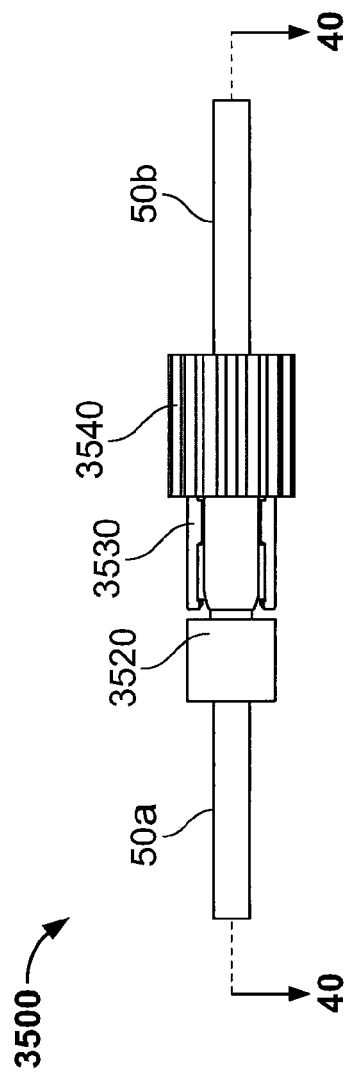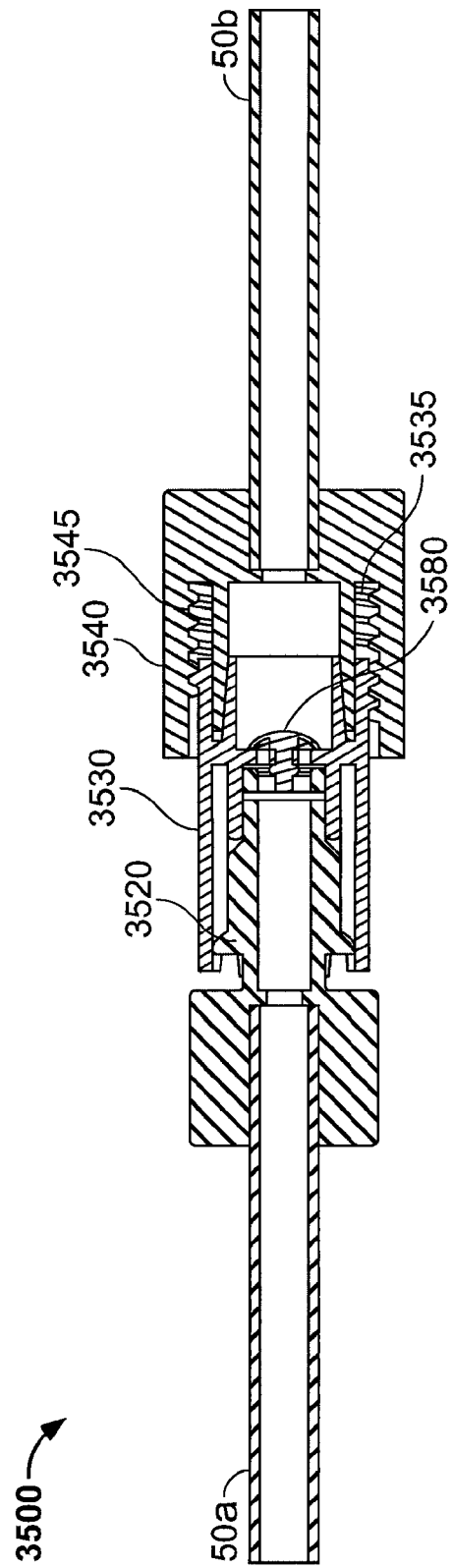
FIG. 39
FIG. 40

FLUID CONDUIT CONNECTION

TECHNICAL FIELD

This description relates to fluid conduit connection.

BACKGROUND

Many diagnostic and operative surgical procedures, such as arthroscopic procedures, require the delivery of sterile irrigation fluid to an articular joint body cavity during the course of the surgical procedure. The irrigation fluid maintains distension of the articular cavity and ensures clear visualization of the articular space during the procedure. The irrigation fluid is pumped from an irrigation source, such as a fluid bag, through various interconnected tubing delivery sets to the articular joint body cavity.

Irrigation fluid can be delivered from the fluid source to the articular joint body cavity using a single-use sterile tubing set. The tubing set includes, for example, a pumping mechanism, intravenous bag spikes, plastic tubing, pinch clamps and a distal-end instrument connector, that connects to an arthroscopic inflow instrument. At the conclusion of the surgical procedure the entire tubing set, including the pumping mechanism, is typically disposed to maintain an aseptic operating environment.

Alternatively, irrigation fluid can be delivered from the fluid source through a reusable section (day-set) and a single-use, disposable section (patient-set). The day-set is typically intended to be used for one day with different patients and includes the pumping mechanism connected to a reusable tubing set (day-side tubing set). The day-side tubing set is connected to an inflow tubing set (patient set) for delivering fluid to the joint body cavity. The patient set is non-reusable and is changed on a per patient basis. The patient set includes a one-way check valve intended to prevent backflow into the reusable day set, such that the patient does not become contaminated.

SUMMARY

According to one general aspect, a fluid connector assembly provides a surgeon with a device for easily and rapidly connecting and disconnecting patients sets to and from day sets. The fluid connector assembly preferably maintains an aseptic surgical environment by avoiding unacceptable contamination of the day set both during a surgical procedure and when the day set is not connected to a patient set.

According to another general aspect, a fluid conduit connector assembly includes a connector having a body with an inner surface defining a fluid channel. The fluid conduit connector assembly also includes an inlet region for flow of fluid into the fluid channel, and an outlet region for flow of fluid from the fluid channel. The connector further includes an axial alignment member outward of the body, and a pair of flexible tabs arranged generally circumferentially of the alignment member and outward of the body.

Implementations of this aspect may include one or more of the following features. For example, the fluid connector assembly includes an annular flange connecting the alignment member and the tabs. The connector assembly includes an opposing axial alignment member outward of the body. The alignment members are rails. The outlet region of the body has an outer surface that defines an annular groove, and there is an O-ring within the groove. The inlet region of the body has an outer surface defining an annular groove, and there is an O-ring within the groove. The connector includes a check valve.

The connector includes a patient-side connector and a transfer member. The transfer member has a body with an inner surface defining a fluid channel. The transfer member includes an inlet region for flow of fluid into the fluid channel, and an outlet region for flow of fluid from the fluid channel. The transfer member further includes an axial alignment member outward of the body, and a pair of flexible tabs arranged generally circumferentially of the alignment member and outward of the body. The transfer member includes a check valve. The transfer member includes an opposing axial alignment member outward of the body. The transfer member alignment members face inward, and the transfer member includes an opposing pair of alignment members facing outward.

The connector assembly includes a day-side connector. The transfer member is releasably attachable to the day-side connector and the patient-side connector. The day-side connector includes a body with an inner surface defining a fluid channel. The day-side connector also includes an inlet region for flow of fluid into the fluid channel, and an outlet region for flow of fluid from the fluid channel. The day-side connector further includes an axial alignment member outward of the body, and a pair of flexible tabs arranged generally circumferentially of the alignment member and outward of the body. Each of the alignment members and each of the tabs are aligned such that the day-side connector, the patient-side connector, and the transfer member can be attached by sliding the alignment members relative to each other, and detached by pressing on respective tabs.

According to another general aspect, a fluid conduit connector assembly includes a day-side connector that has a pair of flexible tabs, a patient-side connector that has a pair of flexible tabs, and a transfer member that has a pair of flexible tabs. The three pairs of tabs are configured such that the transfer member releasably couples the day-side and patient-side connectors.

Implementations of this aspect may include one or more of the following features. For example, the day-side connector, the patient-side connector and the transfer member each include an alignment member. When coupled, the alignment members cause the three pairs of tabs to align.

According to another general aspect, a method for aseptically connecting a fluid conduit includes coupling a first fluid connector having a first fluid outlet and a releasable transfer member to a second fluid connector having a second fluid outlet to form a leak resistant fluid connection. The transfer member is coupled in a position intermediate to the first fluid outlet and the second fluid outlet, and includes a check valve for controlling flow in a direction from the first fluid outlet toward the second fluid outlet. The method also includes removing the first fluid connector from the transfer member and the second fluid connector, where the transfer member and the second fluid connector retain the leak resistant fluid connection.

The details of one or more embodiments are set forth in the accompanying drawings and the description below. Other features, objects, and advantages will be apparent from the description and drawings, and from the claims.

DESCRIPTION OF DRAWINGS

FIGS. 29A-D are perspective view of a fluid conduit connector assembly according to another embodiment.

FIG. 39 is a side view of the fluid conduit connector assembly of FIG. 35 with the day-side tubing connector operatively connected to the transfer cap and patient-side tubing connector.

FIG. 40 is a sectional view of the fluid conduit connector assembly taken along line 40-40 in FIG. 39.

Like reference symbols in the various drawings indicate like elements.

DETAILED DESCRIPTION

Figure 1:
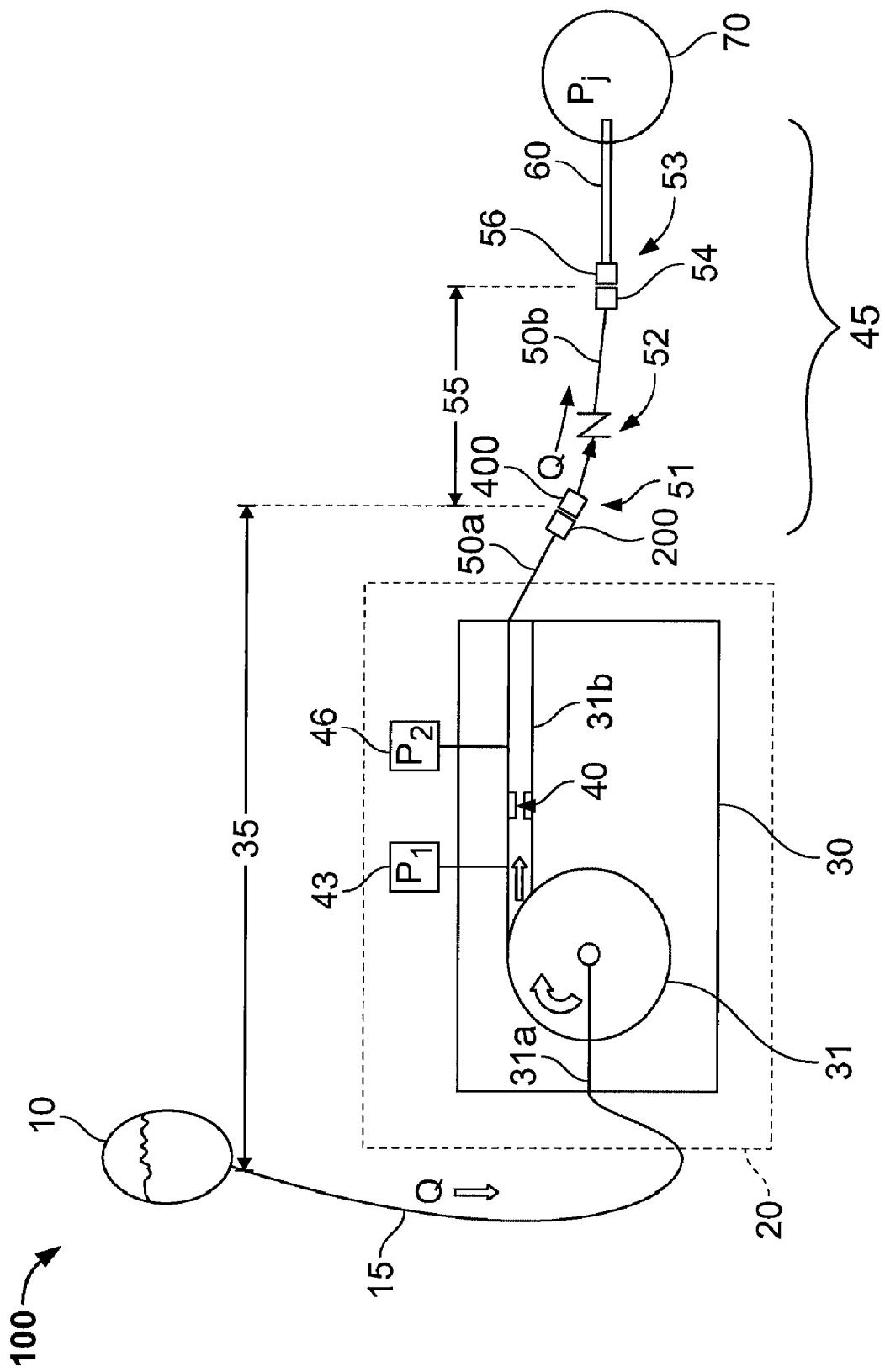
FIG. 1 is a schematic view of a fluid management system.

Referring to FIG. 1, a fluid conduit connector assembly 51 for connecting patient tubing to day tubing in a fluid management system 100, such as the fluid management system described in U.S. patent application Ser. No. 11/423,899, filed Jun. 13, 2006, the entirety of which is incorporated by reference herein, includes a first connector 200 and second connector 400. The fluid management system 100 includes an outlet conduit 45 formed by sections of surgical tubing 50a, 50b, which are connected by connector assembly 51. The system 100 also includes a check valve 52 located in surgical tubing section 50b. In addition, the system 100 includes a surgical tubing connector 53, such as male and female luer connectors or another suitable connector assembly, connecting the surgical tubing section 50b to a cannula 60. The cannula typically is made of steel or plastic.

The fluid management system 100 includes a day-side set 35 of components (including, for example, first connector 200, a pump cassette 30, control unit 20, day-side surgical tubing section 50a, and inlet conduit 15) and a patient-side set 55 of components (including, for example, second connector 400, patient-side surgical tubing section 50b, check valve 52, and surgical tubing connector 54). The day-side set 35 and the patient-side set 55 are connected to each other by the fluid conduit connector assembly 51. The day-side set 35 generally includes reusable components, e.g., that can be used for multiple procedures or patients, such as the pump cassette 30 or day-side surgical tubing section 50a. The patient-side set 55 includes single-use components that are generally disposed of after a surgical procedure and are used for only a single patient, such as the surgical tubing connector 54 and patient-side surgical tubing section 50b.

Figure 2:
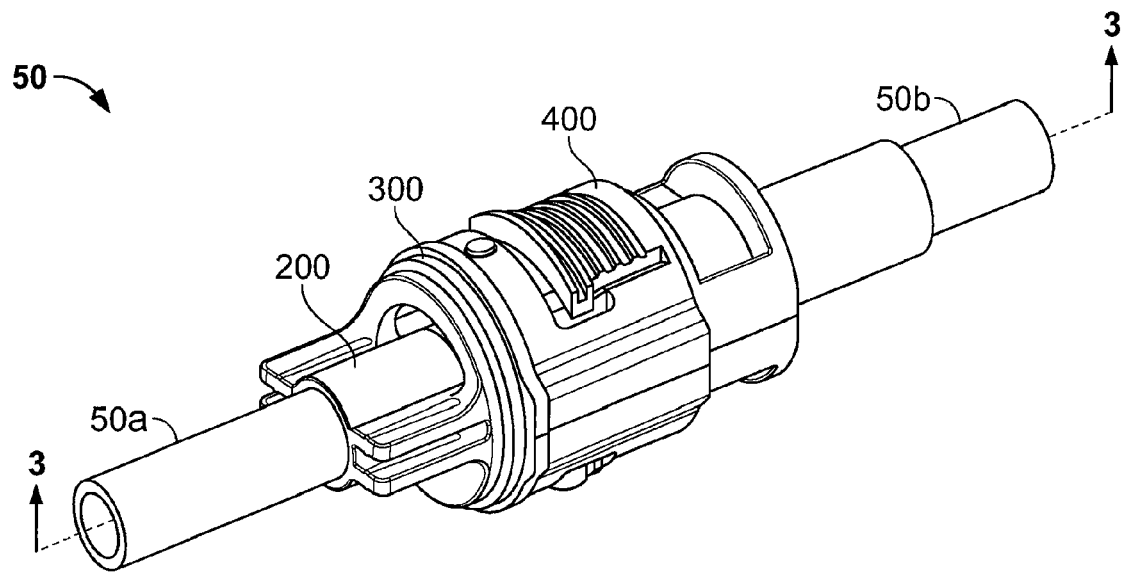
FIG. 2 is perspective view of a fluid conduit connector assembly.
Figure 3:
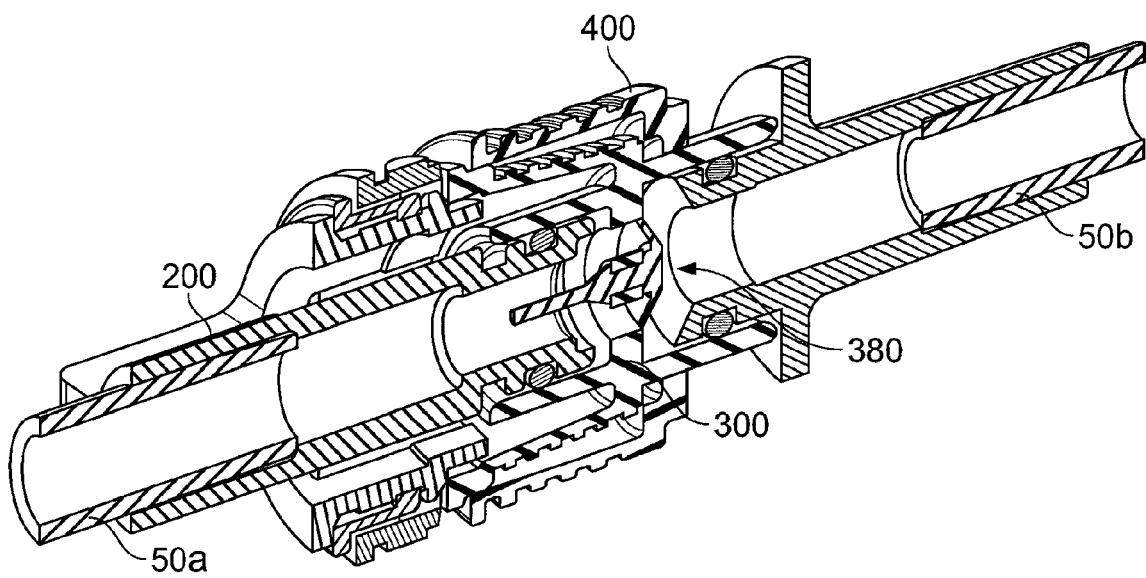
FIG. 3 is a sectional view taken along line 3-3 in FIG. 2.

Referring to FIGS. 2 and 3, the fluid conduit connector assembly 51 connects and disconnects the day-side surgical tubing section 50a with the patient-side surgical tubing section 50b. The fluid conduit connector assembly 51 includes the day-side connector 200, a transfer member or cap 300, and the patient-side connector 400. The transfer cap 300 fits over the day-side connector 200 with a female-male fit and within the patient-side connector 400 with a male-female fit. Accordingly, surgical fluid flows along a fluid path defined by the day-side surgical tubing section 50a, the day-side connector 200, the transfer cap 300, the patient-side connector 400, and the patient-side surgical tubing section 50b. The transfer cap 300 includes a one-way check valve 380 that permits fluid flow from the day-side set 35 to the patient-side set 55.

Figure 10:
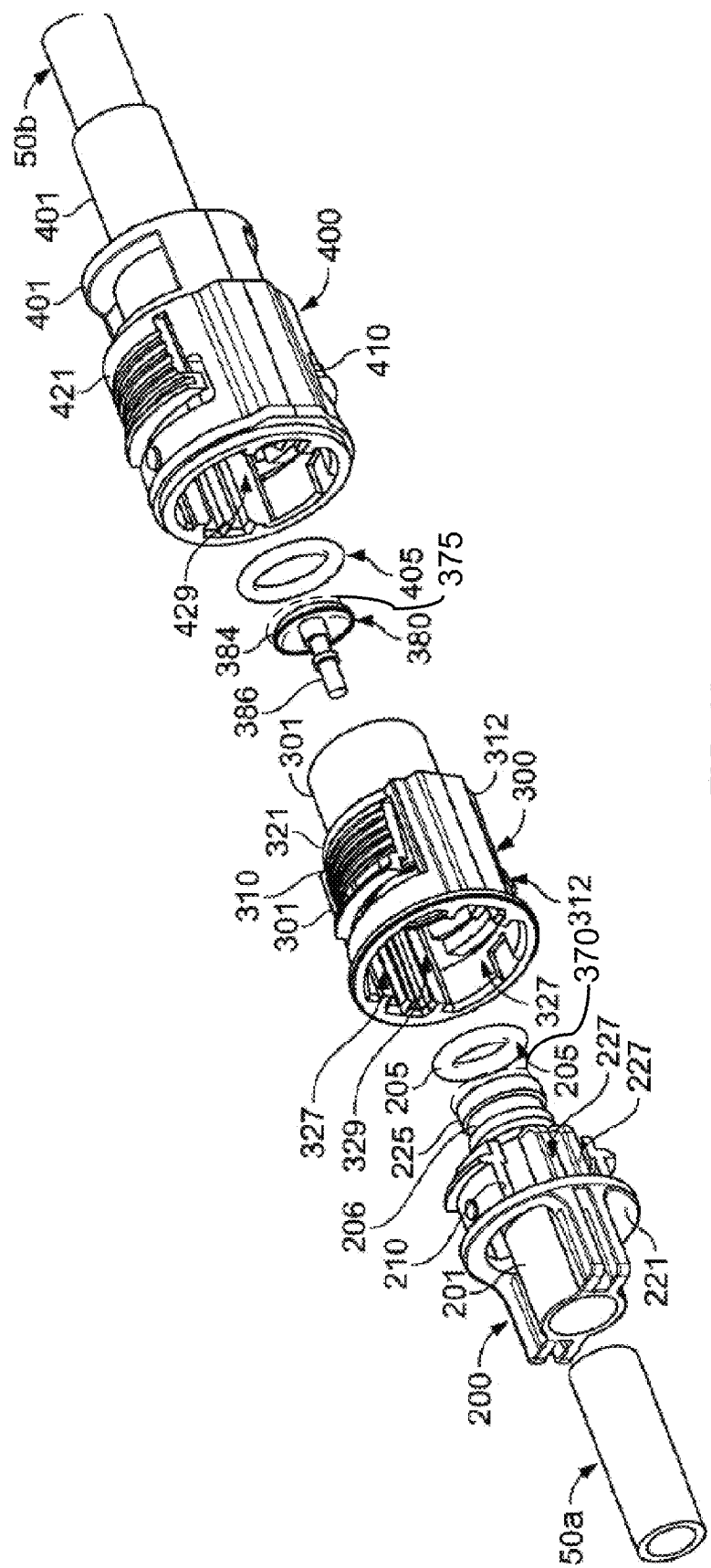
FIG. 10 is an exploded perspective view of the fluid conduit connector assembly of FIG. 8.
Figure 11:
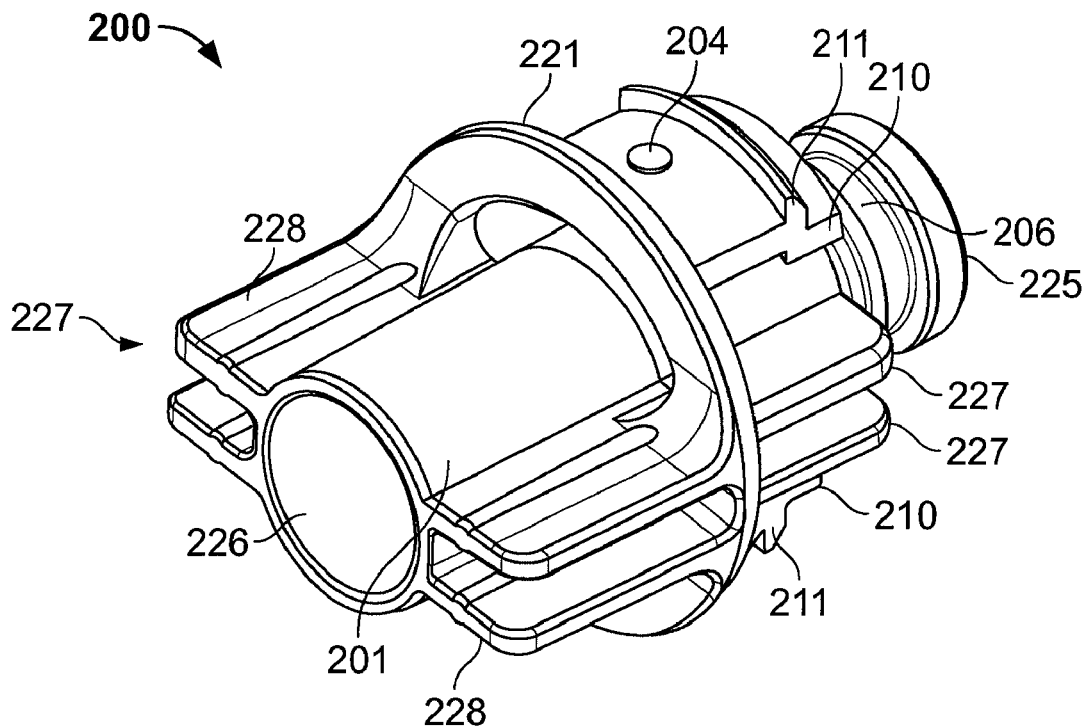
FIG. 11 is a perspective view of the day-side tubing connector.
Figure 12:
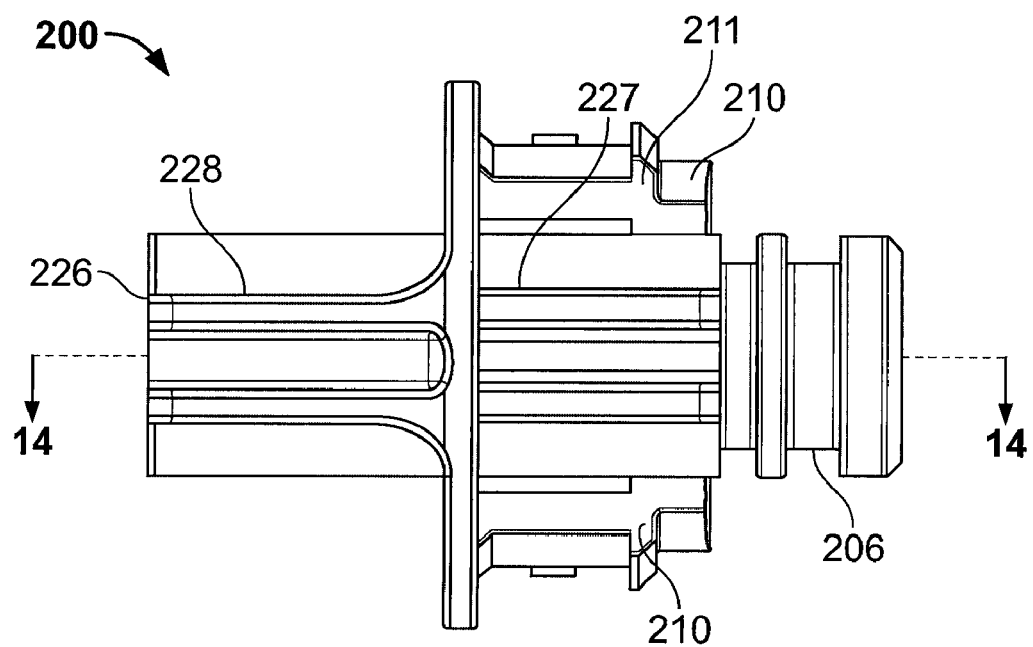
FIG. 12 is a side view of the day-side tubing connector of FIG. 11.
Figure 13:
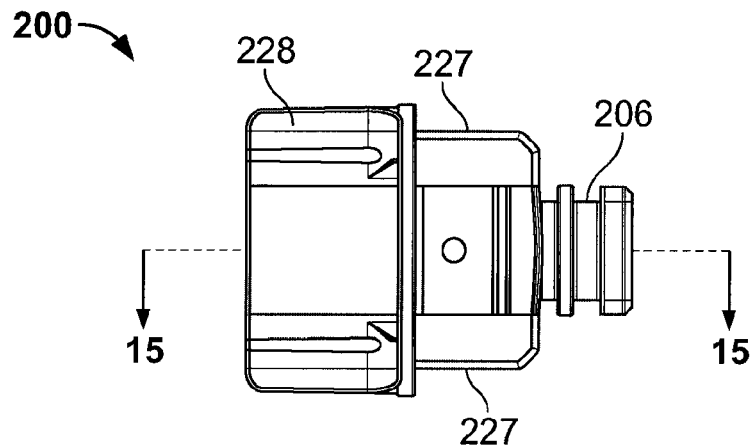
FIG. 13 is a plan view of the day-side tubing connector of FIG. 11.
Figure 14:
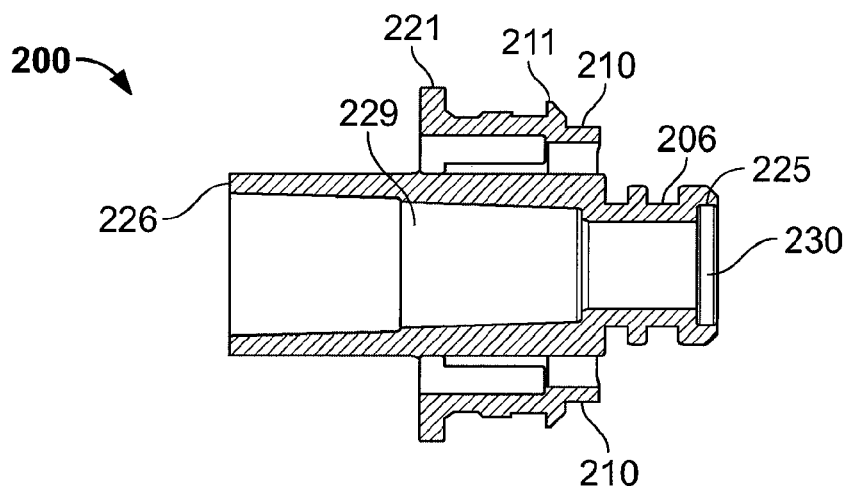
FIG. 14 is a sectional view of the day-side tubing connector taken along line 14-14 in FIG. 12.
Figure 15:
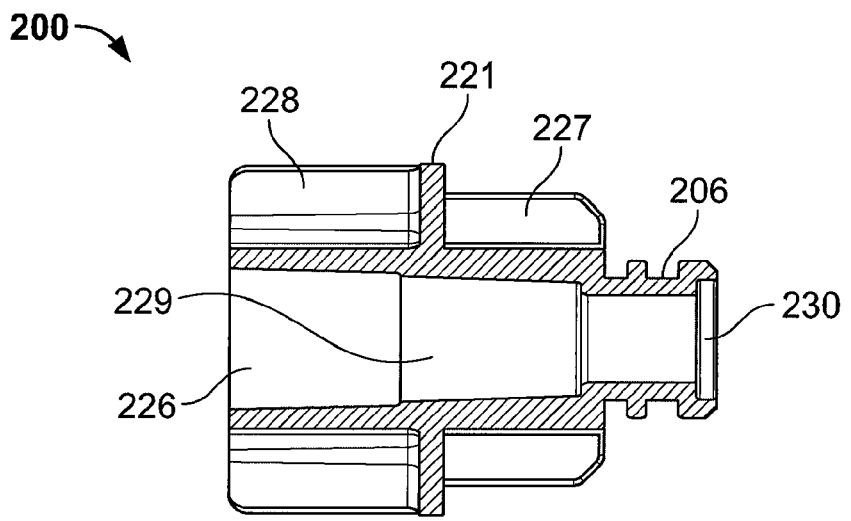
FIG. 15 is a sectional view of the day-side tubing connector taken along line 15-15 in FIG. 13.
Figure 16:
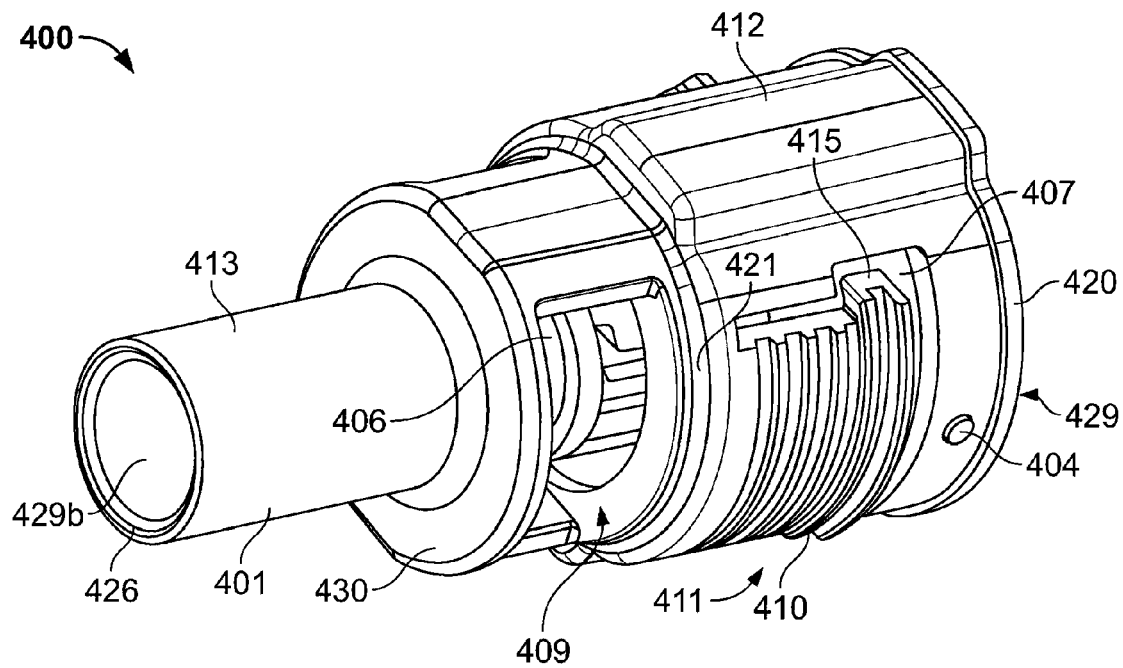
FIG. 16 is a perspective view of the patient-side tubing connector shown without being connected to a transfer cap.
Figure 17:
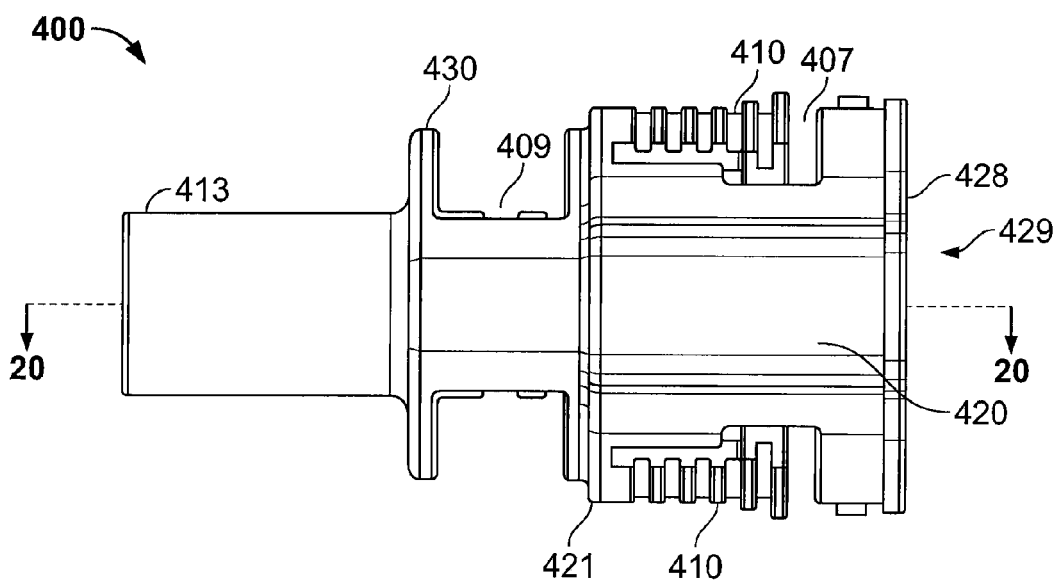
FIG. 17 is a plan view of the patient-side tubing connector of FIG. 16.
Figure 18:
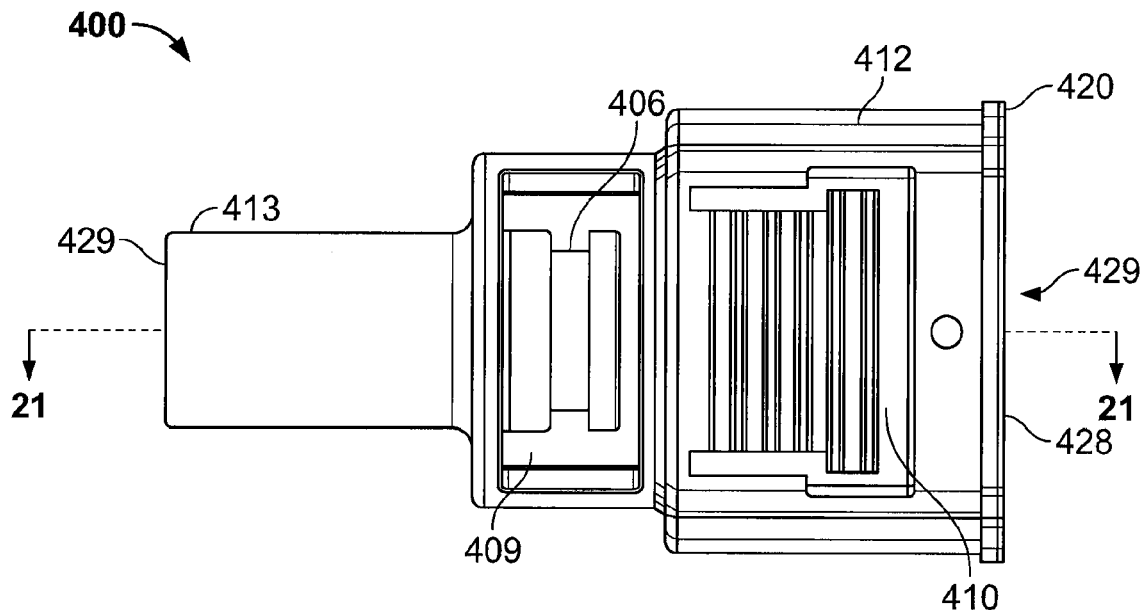
FIG. 18 is a side view of the patient-side tubing connector of FIG. 16.
Figure 19:
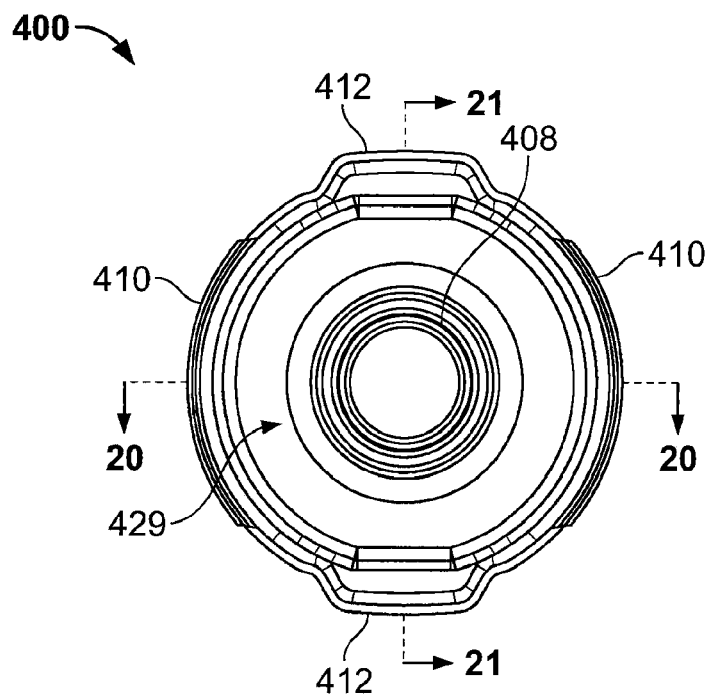
FIG. 19 is an end view of the patient-side tubing connector.
Figure 20:
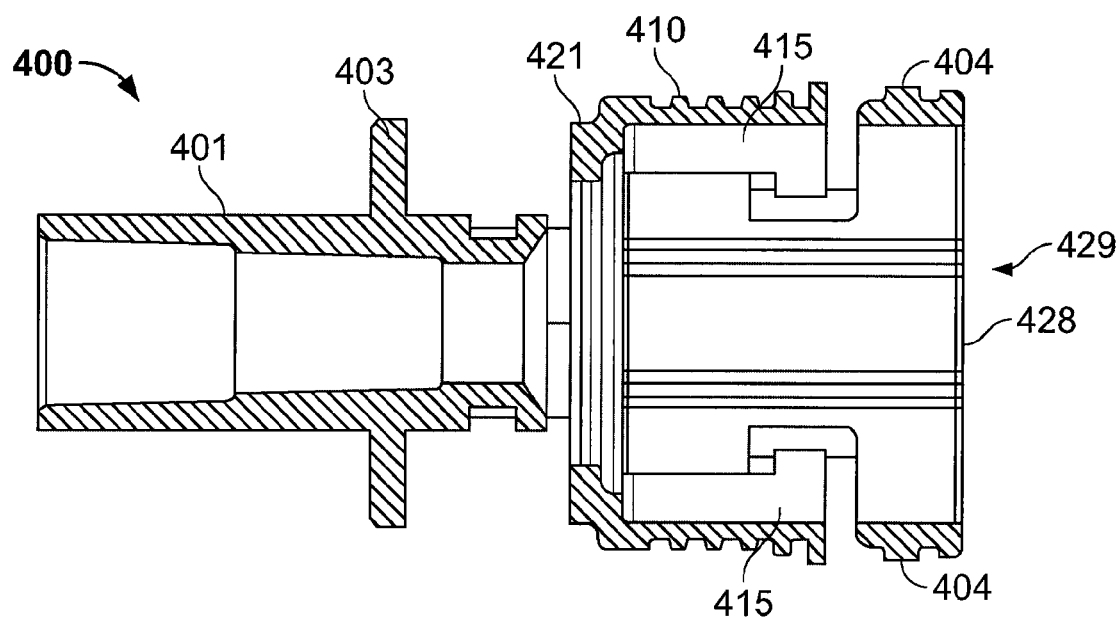
FIG. 20 is a sectional view of the patient-side tubing connector taken along line 20-20 in FIG. 17.
Figure 21:
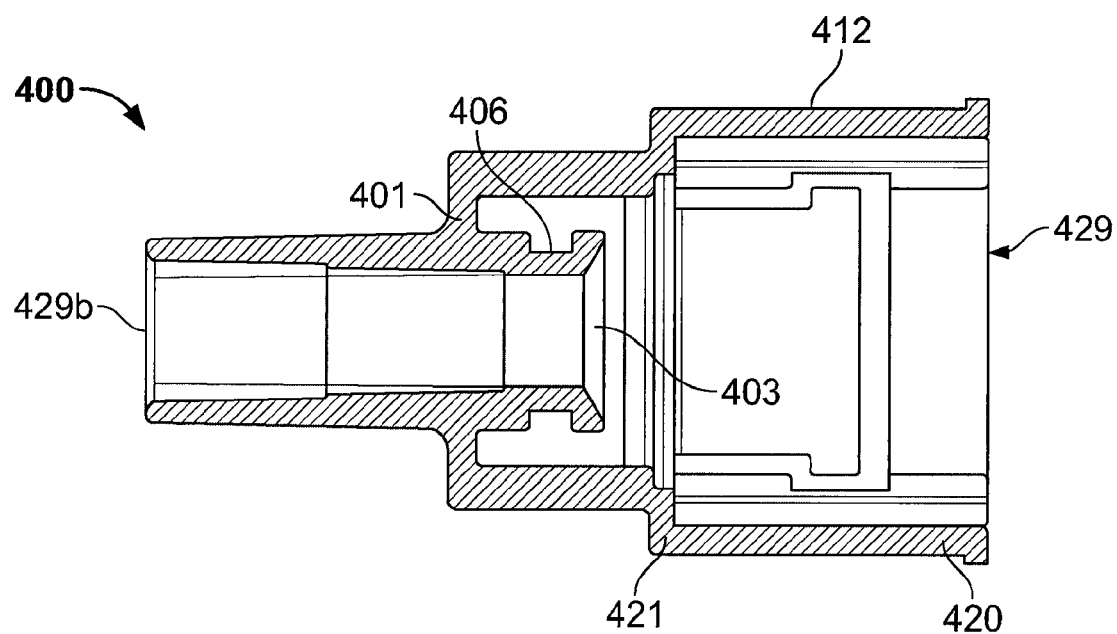
FIG. 21 is a sectional view of the patient-side tubing connector taken along line 21-21 in FIG. 18.
Figure 22:
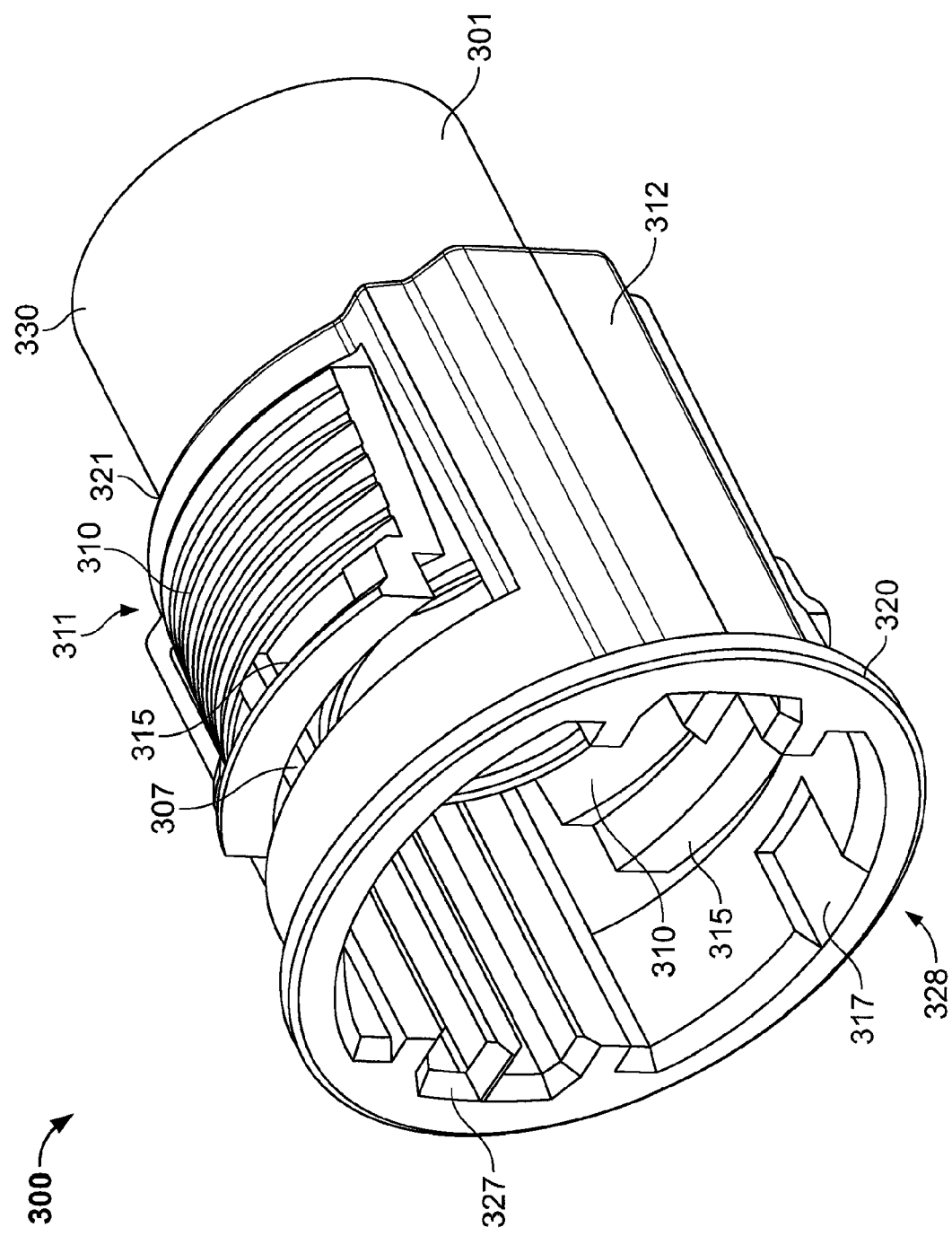
FIG. 22 is a perspective view of a transfer cap.
Figure 23:
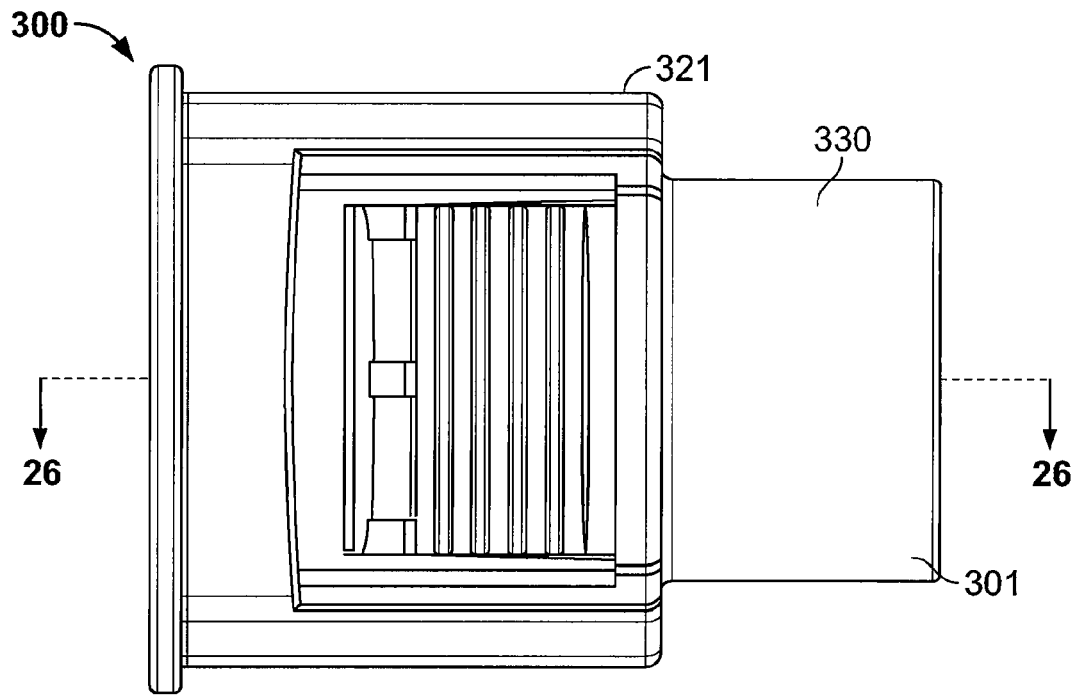
FIG. 23 is a side view of the transfer cap of FIG. 22.
Figure 24:
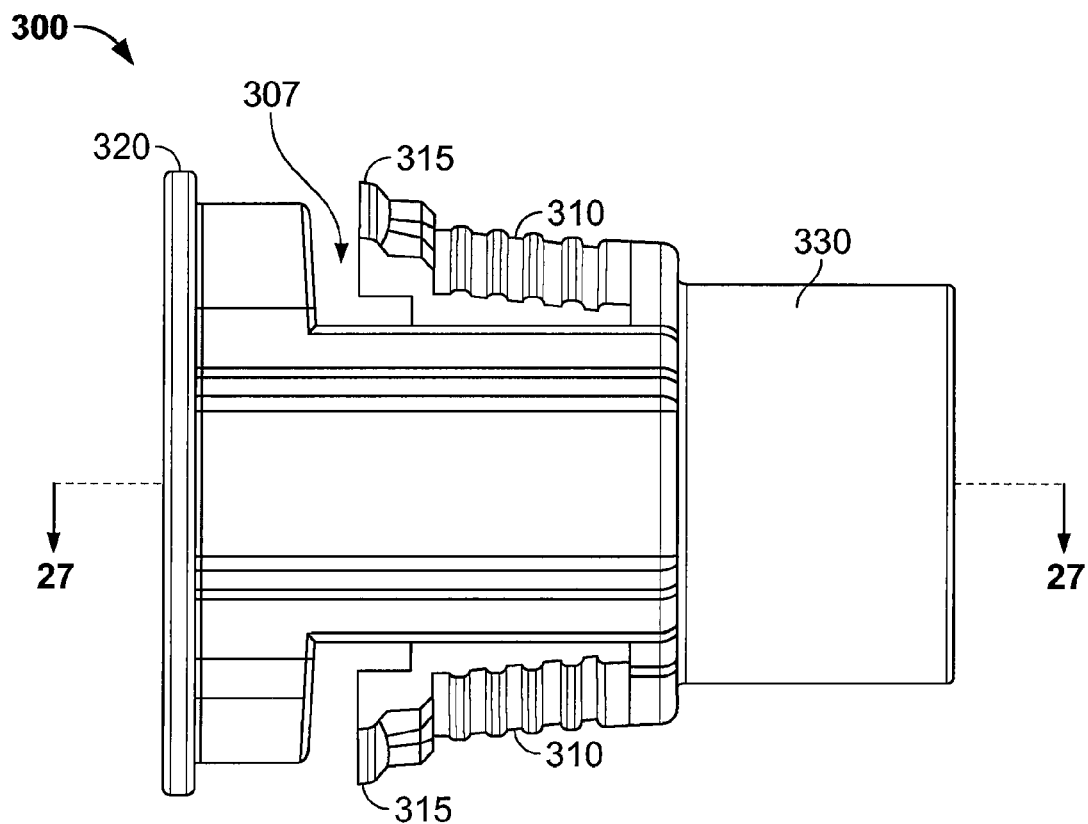
FIG. 24 is a plan view of the transfer cap of FIG. 22.

Referring to FIG. 10, the day-side connector 200, transfer cap 300, and patient-side connector 400 each includes at least one alignment member. Connector 200, which is shown in more detail in FIG. 11, has a pair of alignment rails 227 (only one of which is visible in FIG. 10), and transfer cap 300, which is shown in more detail in FIG. 22, has a pair of alignment grooves 327 for receiving the rails. Transfer cap 300 also has a pair of alignment formations 312, and connector 400 has a pair of alignment grooves 412 for receiving the alignment formations. The day-side connector 200, transfer cap 300, and patient-side connector 400 each also includes a pair of tabs 210, 310, 410, respectively (only one of each pair of tabs being shown in FIG. 10.) Each of the alignment members and each of the tabs are aligned such that the day-side connector, the patient-side connector, and the transfer member can be attached by sliding the alignment members relative to each other, and detached by pressing on respective tabs. The day-side connector tabs 210 include raised leading ends 211 (shown in FIG. 11) that operatively fit within a recess 307 (shown in FIG. 22) defined by the tabs 310 of the transfer cap 300. The transfer cap tabs 310 include raised leading ends 315 (shown in FIG. 22) that operatively fit within a recess 407 (shown in FIG. 16) defined by the tabs 415 (shown in FIG. 16) of the patient side connector 400.

Figure 4:
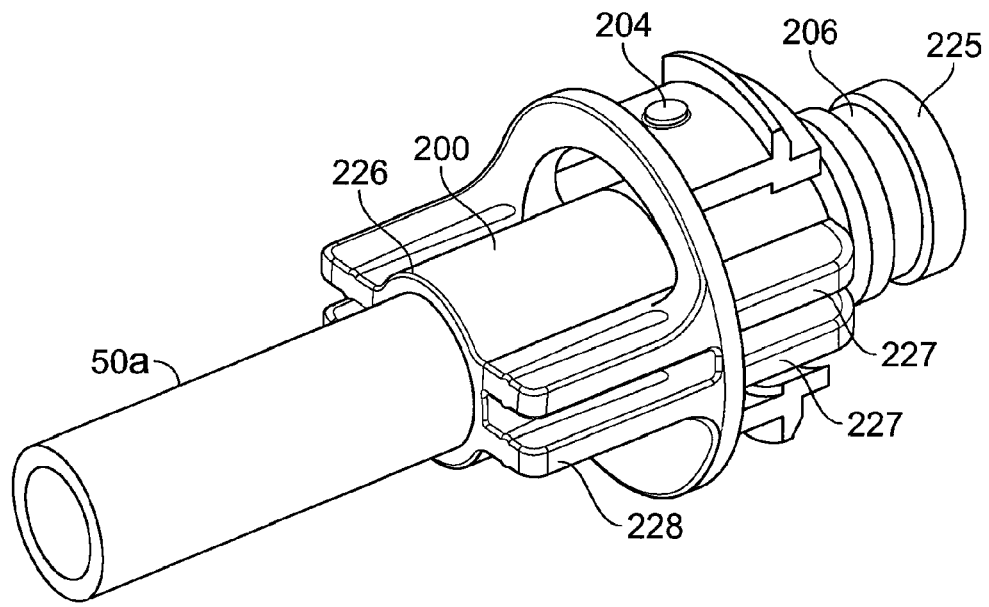
FIG. 4 is a perspective view of a day-side tubing connector.
Figure 5:
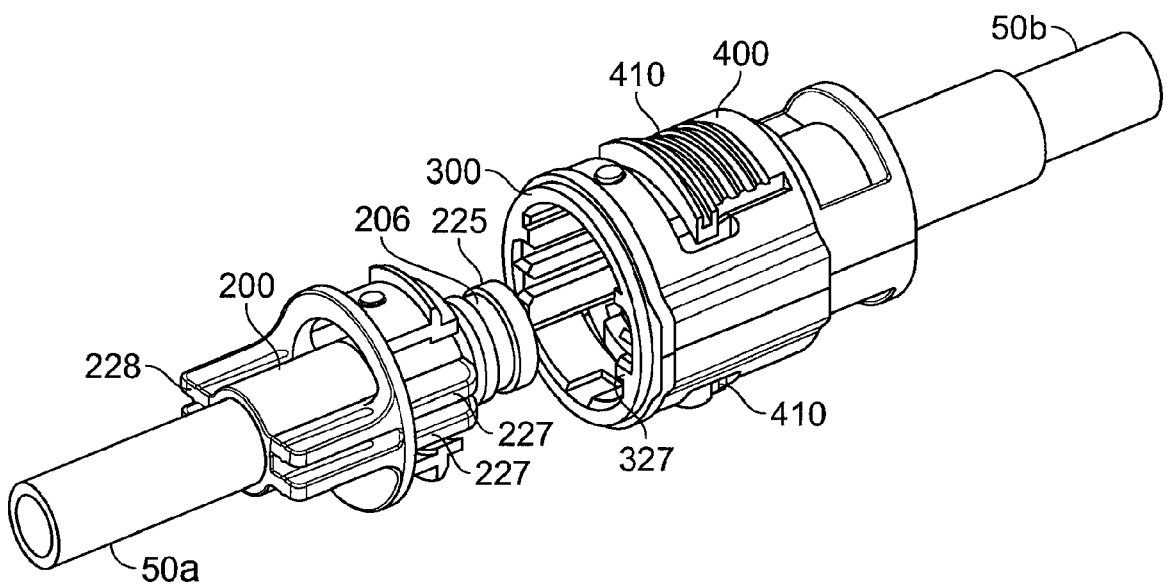
FIG. 5 is a perspective view of a transfer cap and patient-side tubing connector aligned for connection with the day-side tubing connector of FIG. 4.
Figure 6:
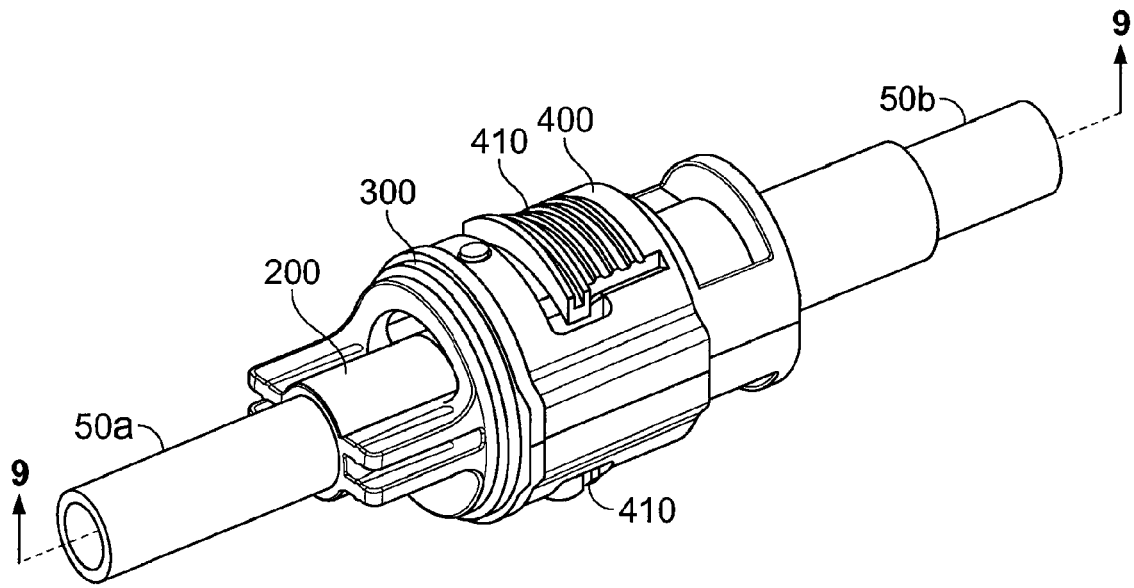
FIG. 6 is a perspective view of the transfer cap and patient-side tubing connector connected with the day-side tubing connector of FIG. 4.

Referring to FIGS. 4-7, a process of connecting the patient-side set 55 to the day-side set 35 includes connecting the patient-side connector 400 to the day-side connector 200 by way of the releasable transfer cap 300 (FIGS. 4 and 5). The transfer cap 300 is initially secured to the patient-side connector 400 by fitting the annular outlet opening 330 and annular outlet flange 321 within the internal cavity 429 (see FIG. 10) and engaging leading ends 315 of tabs 310 within recesses 407. The day-side connector 200 is attached to the transfer cap 300 by fitting the exposed male connector 225 within the internal cavity 329 (see FIG. 10) and engaging leading ends 211 of tabs 210 within recesses 307.

Referring to FIG. 5, the alignment rails 227 and the alignment grooves 327 ensure that the transfer cap 300 and patient-side connector 400 are properly aligned by medical personnel positioning the patient-side connector 400 and transfer cap 300 in one of only two acceptable, symmetrical alignment positions. The male connector 225 is properly engaged with the transfer cap 300 when the tabs 210 (see FIG. 10) snap-fit within the recesses 307 (see FIG. 22) of the transfer cap 300.

Figure 7:
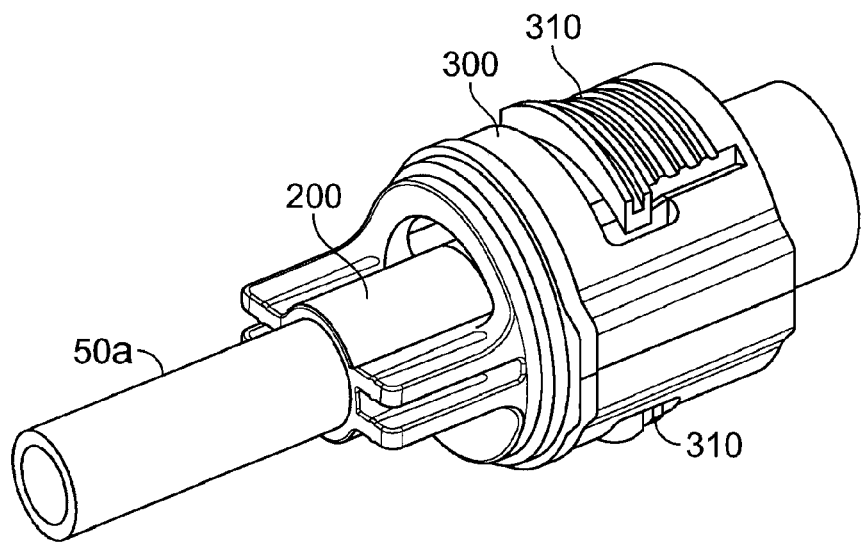
FIG. 7 is a perspective view of the transfer cap operatively connected with the day-side tubing connector and with the patient-side tubing connector removed.

After completion of a surgical procedure, medical personnel release the patient side connector 400 by squeezing the tabs 410 (see FIG. 10) to remove the patient-side connector from the transfer cap 300. Referring to FIG. 7, the transfer cap 300 is left in engagement with the day-side connector 200 to protect the male connector 225 from unnecessary exposure and contact while awaiting the connection of the next patient-side set 55. Medical personnel remove the transfer cap 300 by squeezing the tabs 310 (see FIG. 10) and pulling the transfer cap 300 off of the day-side connector to connect a new patient-side set 55.

Figure 8:
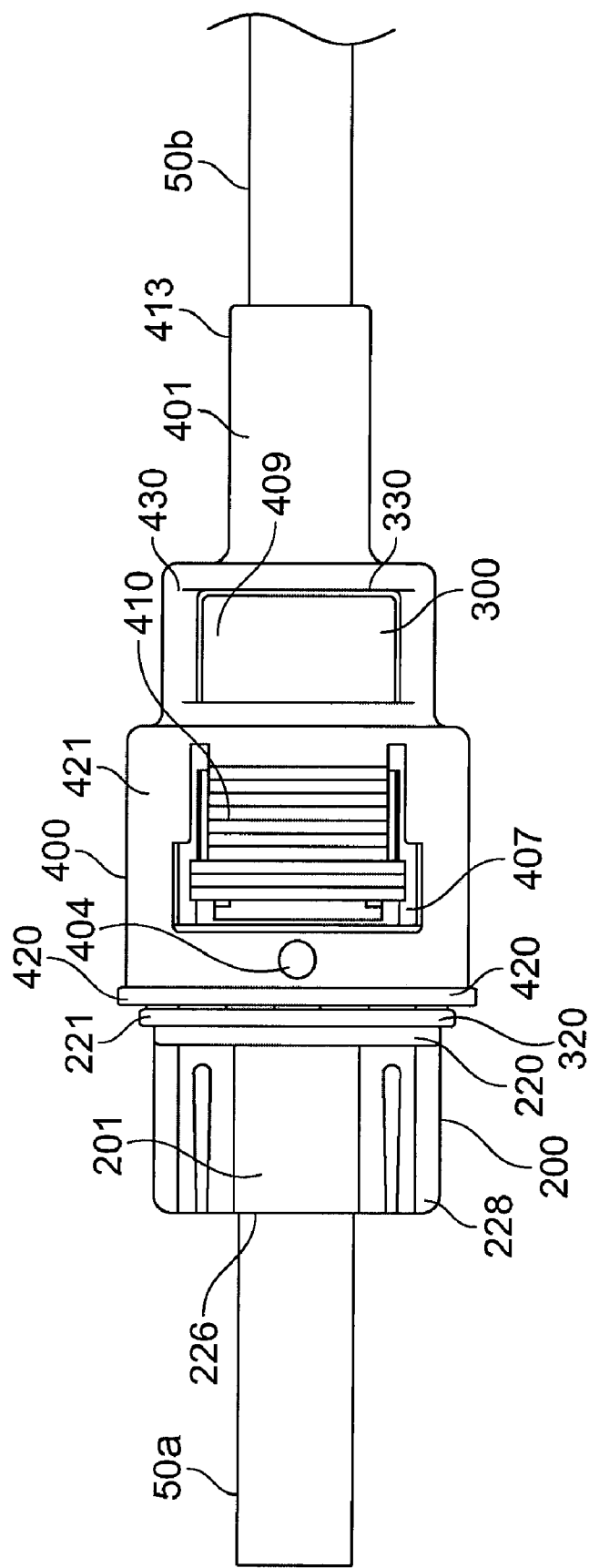
FIG. 8 is a side view of the fluid conduit connector assembly showing the day-side tubing connector operatively connected to the transfer cap and the patient-side tubing connector.
Figure 9:
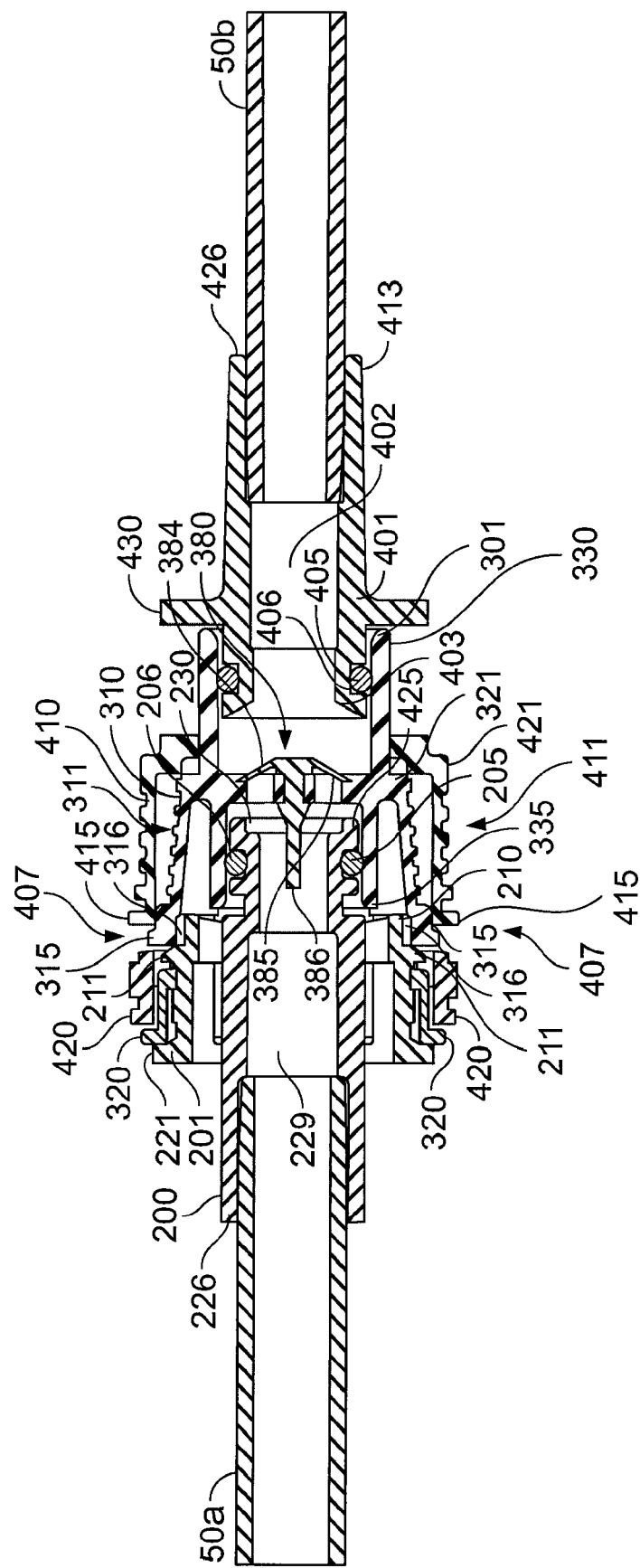
FIG. 9 is a sectional view of the fluid conduit connector assembly taken along line 9-9 in FIG. 6.

Referring to FIGS. 8-10, the day-side connector 200 has a body member 201 including an inlet side 226 that connects to the day-side surgical tubing section 50a, for example, by adhesive bonding, ultrasonic welding or any other suitable connection method. The day-side connector 200 includes an outlet end forming a male connector 225. The male connector 225 can also include an O-ring 205 about its outer circumference secured within an O-ring groove 206. The transfer cap 300 includes a body member 301 defining an internal cavity of the annular inlet opening 335 which receives the male connector 225 of the day-side connector 200 with a snap-fit. The transfer cap 300 includes an annular outlet opening 330 that includes the check valve 380 fitted therein. The patient-side connector 400 includes a body member 401 defining an internal cavity 429 that receives the transfer cap 300 therein with a snap-fit and an annular inlet opening 403. The annular outlet opening 330 fits over the annular inlet opening 403 that also includes an O-ring 405 fitted within an O-ring groove 406 defined by the annular inlet opening 403.

The day-side connector 221, transfer cap 300 and patient-side connector 400 are operatively connected to each other to provide a fluid path between the day-side surgical tubing section 50a and the patient-side surgical tubing section 50b. The day-side connector 200 includes an inlet side 226 defining a tapered tubing conduit 229 for receiving day-side surgical tubing section 50a. The tapered tubing conduit 229 extends axially through the day-side connector 200 and connects with a tapered fluid flow path outlet 230 that connects with the check valve 380 of the adjacent transfer cap 300. The check valve 380 includes a valve stem 386 extending into the tapered fluid flow path outlet 230 and a valve crown 384, which when at equilibrium or under pressure from the patient side seals against a valve seat 385 formed around a periphery of a flanged, annular inlet opening 335 of the transfer cap 300. The valve crown 384 flexes when under pressure from the day side, deforming to unseat from the valve seat 385 to allow fluid flow within the tapered fluid flow path outlet 230 between an open position (see FIG. 3) and a closed position (see FIG. 9). The annular inlet opening 335 and male tubing connection 225 form a fluid tight flow path therebetween. The O-ring 205 is positioned within the O-ring groove 206, which is an annular recess defined by the male tubing connection 225. The valve crown 384 flexes between a seated position (shown in FIG. 9) and an open position (shown in FIG. 3).

Deformation of the valve crown 384 in a downstream direction of the flow path is limited by a flanged, annular inlet opening 403 of the patient-side connector 400. The annular inlet opening 403 and a flanged, annular outlet opening 330 of the transfer cap 300 form a fluid path interface between the transfer cap 300 and the patient-side connector 400. The annular inlet opening 403 defines an O-ring groove 406 which includes an O-ring 405 positioned therein to provide a fluid tight seal between the annular outlet opening 330 and the annular inlet opening 403. Deformation of the valve crown 384 in an upstream direction is limited by the valve seat 385. In addition, the annular inlet opening 403 can include chamfered edges contoured to correspond to a valve crown 384 of the check valve 385 and to reduce flow resistance at the interface between the transfer cap 300 and patient-side connector 400.

Referring to FIGS. 9 and 11-15, the day-side connector 200 includes an annular flange 221 extending radially outward and circumferentially with respect to the body 201. The tabs 210 are connected to the annular flange 221 and extend axially and circumferentially toward the male tubing connector 225. The tabs 210 each include leading ends 211 that protrude radially from the tabs 210 to snap-fit with the recess 307 in the transfer cap 300. The alignment rails 227 are connected to the annular flange 221 and extend axially along and radially outward of the body 201 toward the male tubing connector 225. The alignment rails 227 are circumferentially offset with respect to the tabs 210. The alignment rails 227 extend radially outward from the body to a height sufficient to fit within the corresponding alignment grooves 327 of the transfer cap 300, such as with a sliding friction or interference fit. Accordingly, the alignment rails 227 can extend radially outward of the body less than, equal to, or greater than the tabs 210 with respect to the body 201. The annular flange 221 acts as a depth stop which operatively abuts against the transfer cap 300 to maintain the transfer cap 300 in a proper axial orientation with respect to the day-side connector 200.

Figure 25:
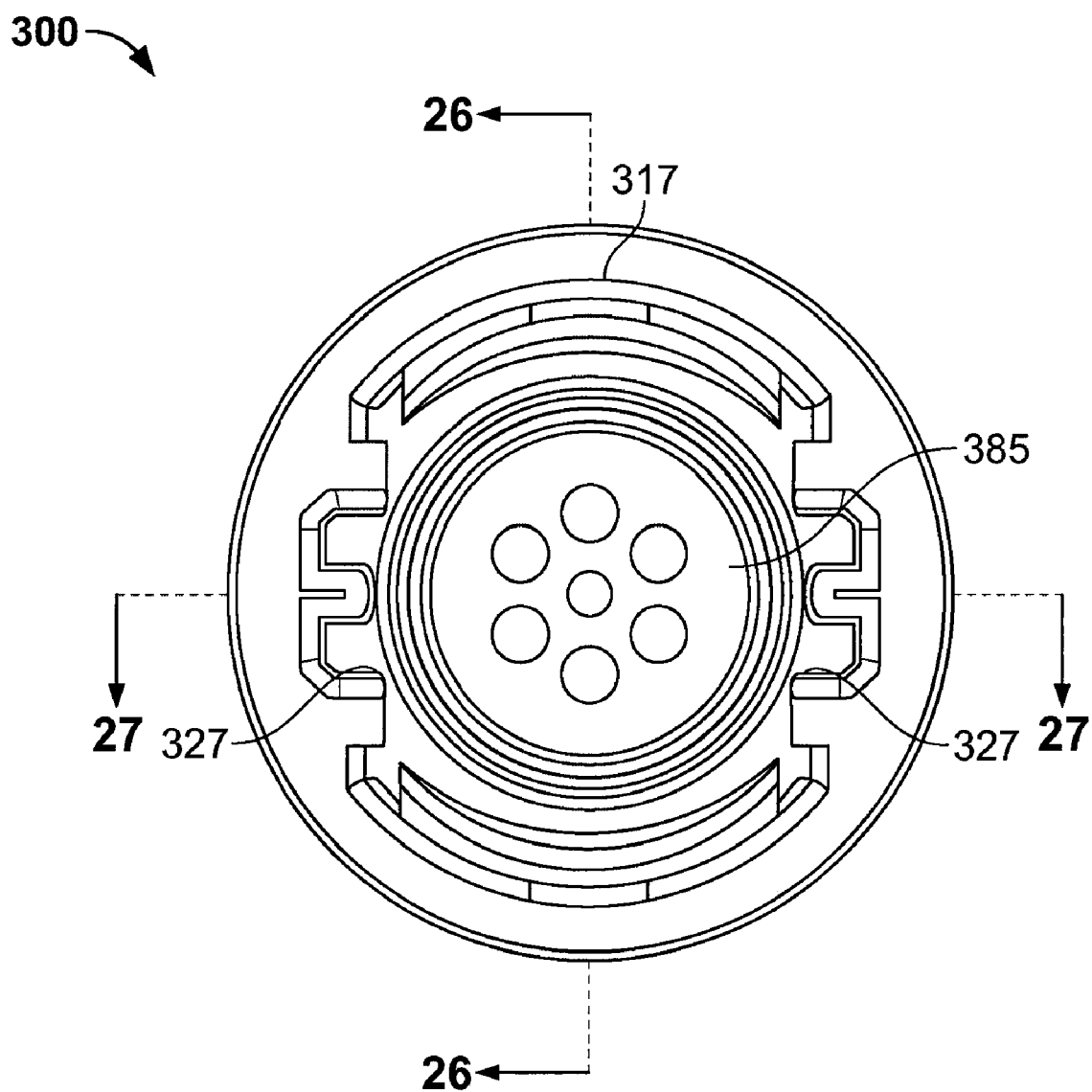
FIG. 25 is an end view of the transfer cap of FIG. 22.
Figure 26:
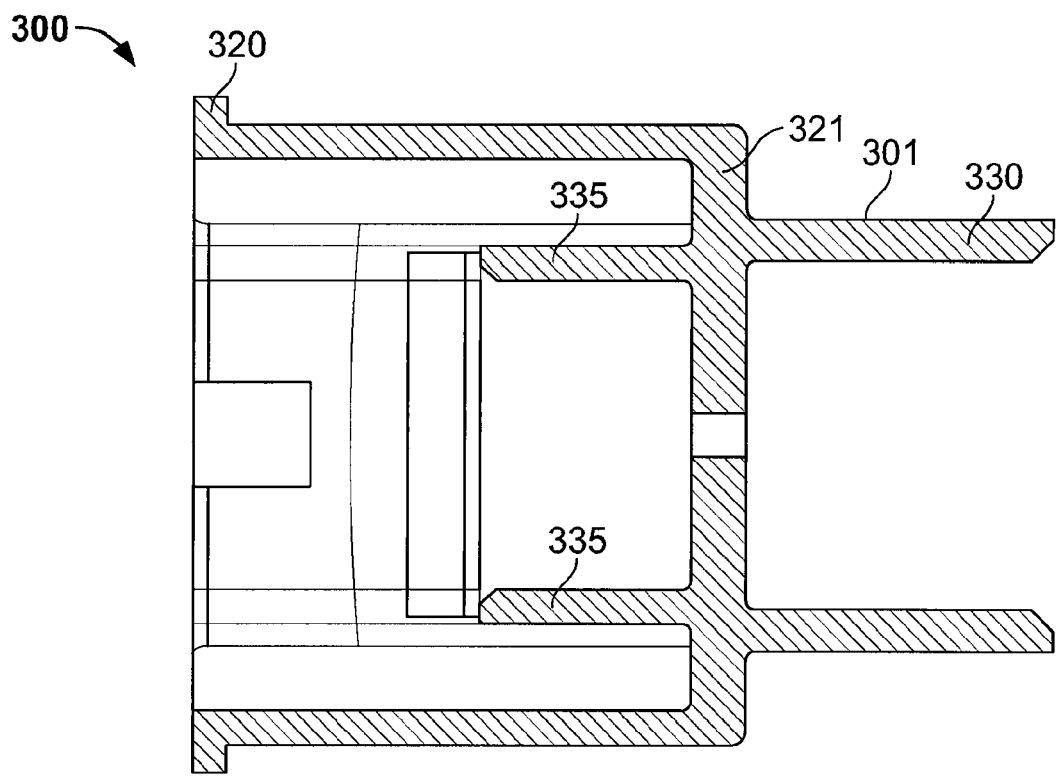
FIG. 26 is a sectional view of the transfer cap taken along line 26-26 in FIG. 23.
Figure 27:
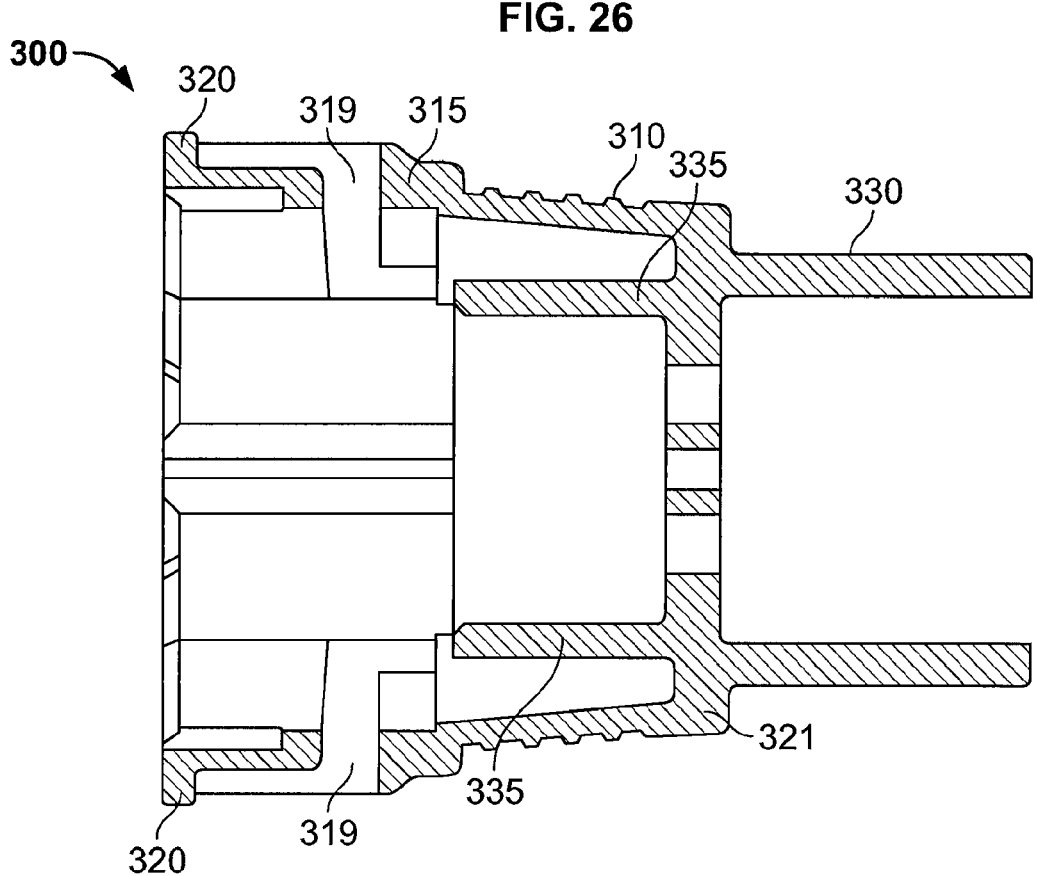
FIG. 27 is a sectional view of the transfer cap taken along line 27-27 in FIG. 24.
Figure 28A:
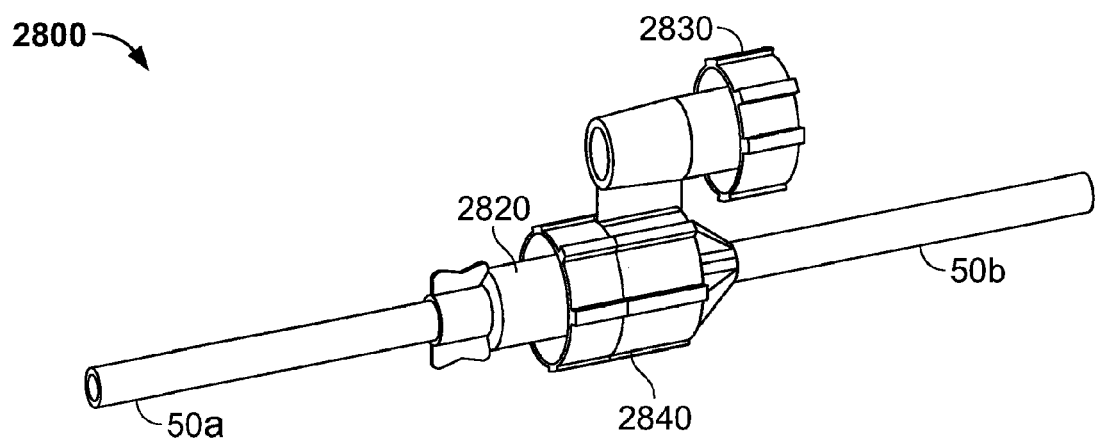
FIGS. 28A-E are perspective views of a fluid conduit connector assembly according to another embodiment.
Figure 28B:
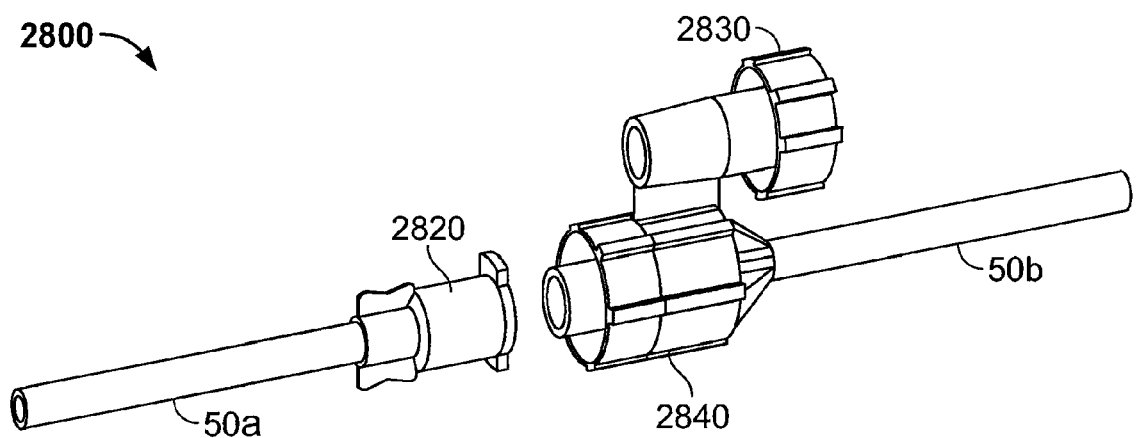
Figure 28C:
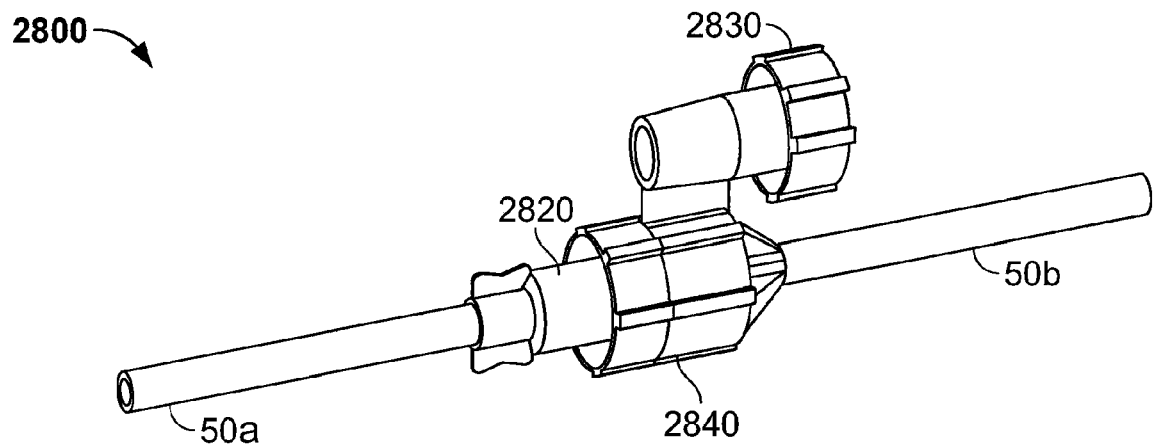
Figure 28D:
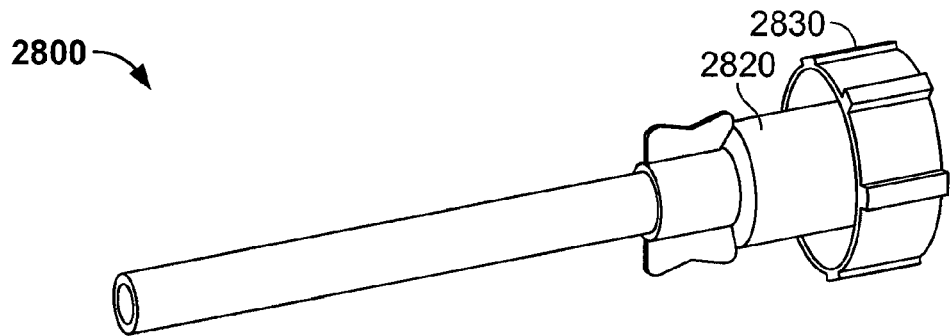
Figure 28E:
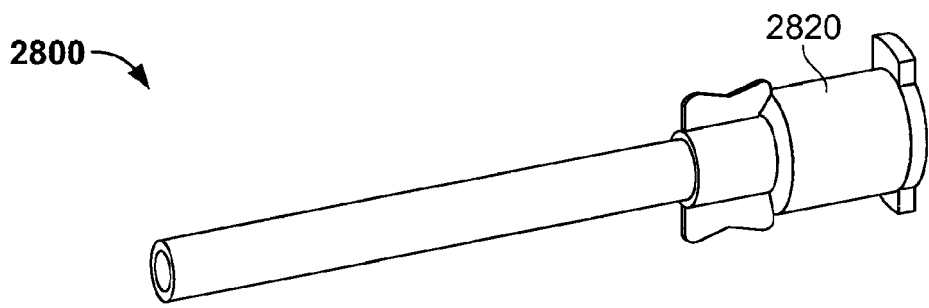
Figure 30:
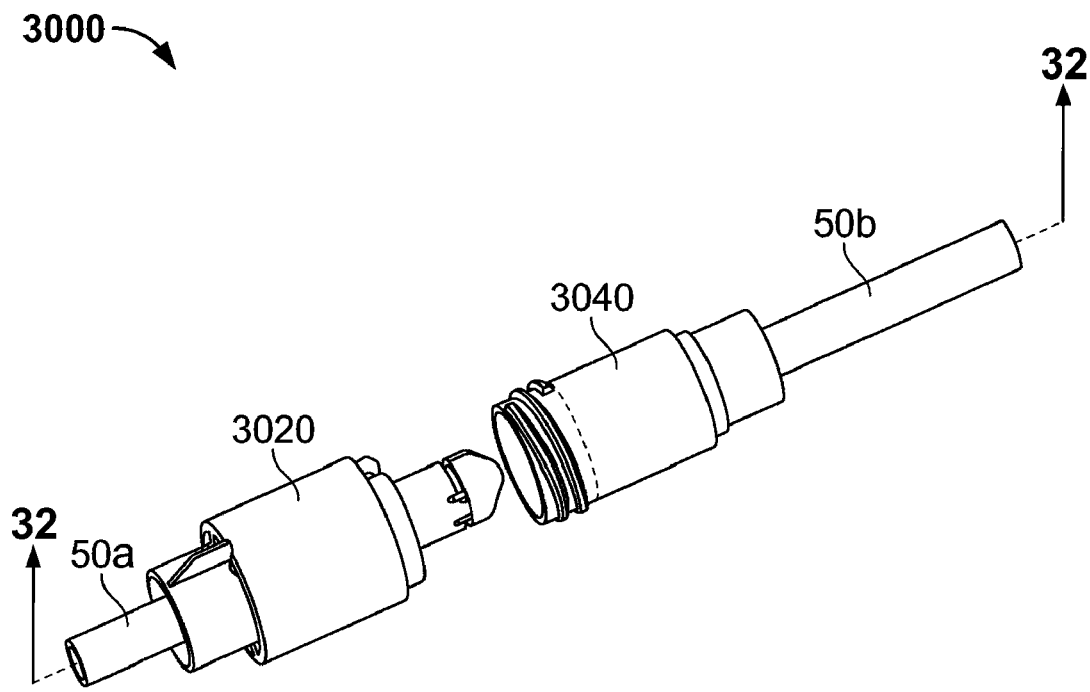
FIG. 30 is a perspective view of a fluid conduit connector assembly according to a another embodiment.
Figure 31:
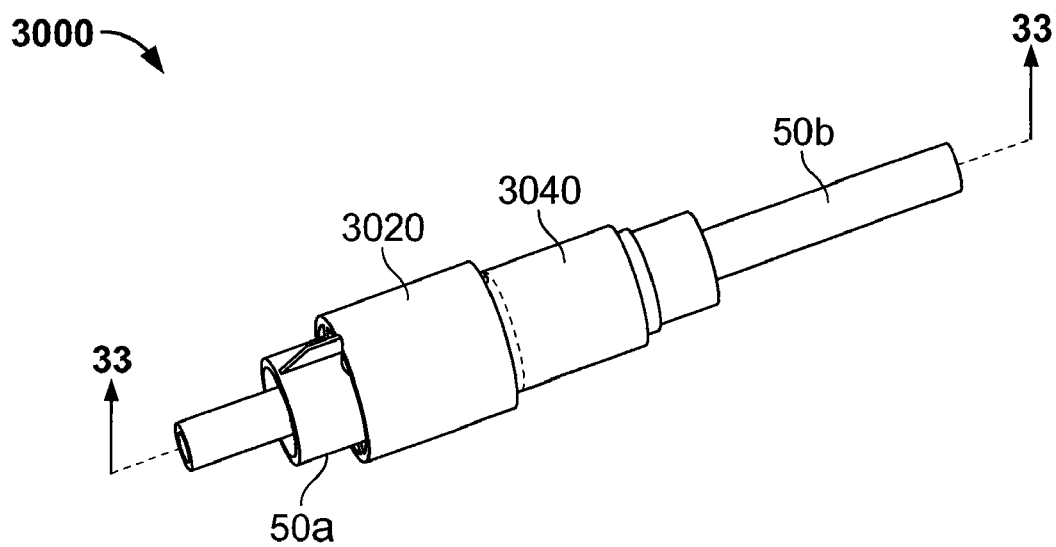
FIG. 31 is a perspective view of the fluid conduit connector assembly of FIG. 30 shown with the day-side tubing connector and the patient-side tubing connector engaged but not operatively connected to permit a flow of fluid therebetween.
Figure 32:
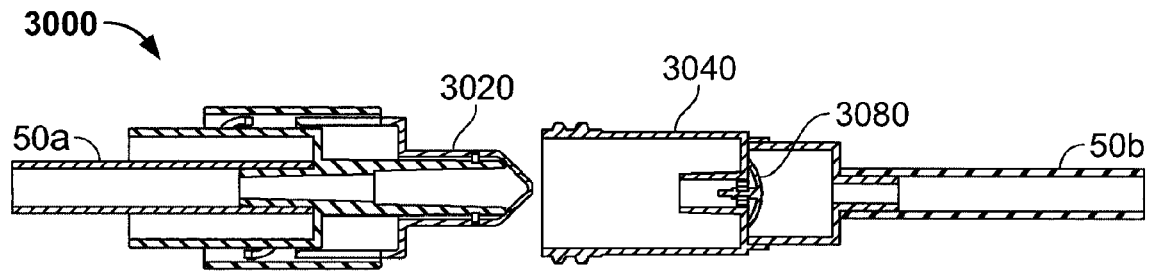
FIG. 32 is a sectional view of the fluid conduit connector assembly taken along line 32-32 in FIG. 30.
Figure 33:
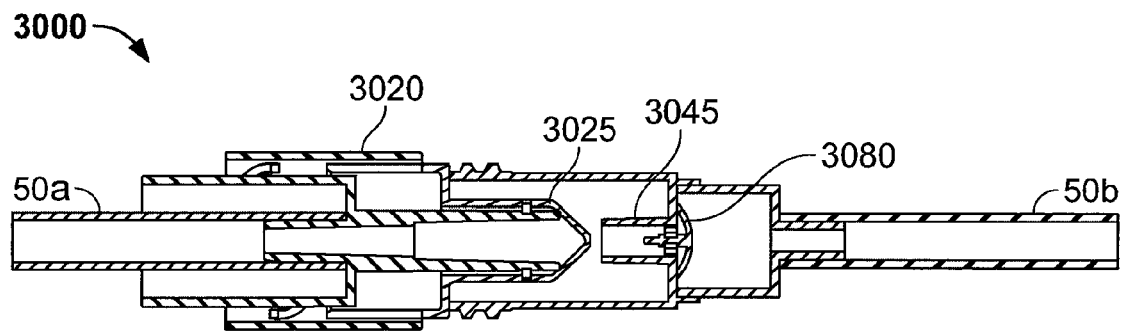
FIG. 33 is a sectional view of the fluid conduit connector assembly taken along line 33-33 in FIG. 31.

Referring to FIGS. 11-15, the tabs 210 act as leaf springs which have an inherent spring bias force that permits the relatively easy compression of the tabs and a snap fit with adjacent quick release tabs 310, 410. The day-side connector 200 also includes optional, elongated rails 228 connected to and extending axially from the annular flange 221 toward an annular inlet opening 226 side of the day-side connector 200. The rails 228 permit a user to easily grasp the day-side connector 200 when connecting and disconnecting the transfer cap 300 and/or patient-side connector 400. In addition, the day-side connector 200 can include an alignment indicator 204 that indicates to a user a proper orientation of the day-side connector 200 with the patient-side connector 400 (and alignment indicator 404 shown in FIG. 16). The alignment indicator 204 is a circular, raised protuberance that fits within a corresponding recess 317 (shown in FIGS. 22 and 25).

Referring to FIGS. 16-21, the patient-side connector 400 includes a body 401 having an annular flange 421 extending radially outward and circumferentially with respect to the body 401. The tabs 410 are connected to the annular flange 421 and extend axially and circumferentially toward outlet opening 428. The outlet opening 428 is defined by an annular flange 420 that operatively abuts against an annular outlet flange 320 of the transfer cap 300. The tabs 410 each include leading ends 415 that protrude radially inward from the tabs 410 to abut against leading ends 315 of the transfer cap 300 when held within the annular opening 428. The outlet flange 420 is connected to a pair of axially extending alignment members 412 that are sized and shaped to correspond to an outer profile of alignment members 312 (FIGS. 22-25) of the transfer cap. The alignment members 412 are circumferentially offset with respect to the tabs 410 and axial centerline CL (FIG. 9).

The patient-side connector 400 includes a window 409 to facilitate molding the O-ring groove 406. The window 409 also allows observation of the connection between the annular outlet opening 330, the annular inlet opening 403 and O-ring 405. The annular outlet opening 330 can be constructed of a relatively transparent material, which allows medical personnel to see the O-ring 405. For example, the annular outlet 330 can be made of clear PVC, polypropylene or any other plastic material with suitable properties, such as being moldable, being bondable to PVC tubing, and having high cycle life.

Referring to FIG. 9, the patient-side connector 400 includes an annular flange 430 which acts as a stop for operatively abutting against a leading edge of the annular outlet opening 330 of the transfer cap 300. The annular inlet opening 403 connects to the tapered, fluid flow outlet 402 of the patient-side connector 400. The tapered, fluid flow outlet 402 extends longitudinally through the patient-side connector 400 and ends at a downstream side of an annular outlet opening 426 of the patient-side connector 400. The tapered fluid flow outlet 402 and tapered fluid flow inlet 229 can each be provided with a gradually tapering surface for facilitating the easy insertion and securing of leading ends of the surgical tubing connections 50a, 50b. In addition, or in the alternative, the tapered, fluid flow outlet 426 and fluid flow outlet 226 can be secured to the tubing with an adhesive and/or by ultrasonic welding.

Referring to FIGS. 16-21, the annular flange 421 and opening 428 define an annular, internal cavity 429 that is contoured to generally correspond to the outer peripheral edges of the transfer cap 300 releasably held therein. The alignment member 412 include a pair of raised, trapezoidally shaped grooves that are shaped to correspond to the outer contours of the alignment rails 227 and raised, trapezoidally shaped grooves (312 shown in FIGS. 22-25e) that operatively fit therein. The grooves 412 provide a relatively smooth profile to the outer periphery of the fluid conduit connector assembly 51 and act as alignment grooves ensuring that the transfer cap 300 and/or day-side connector 200 are properly positioned and fitted within the cavity 429. The annular outlet opening 426 is defined by an annular conduit 413 which also defines the internal, tapered fluid flow outlet 402. The quick release tabs 410 are only partially secured along a first edge of the generally rectangular member so that the tabs 410 are relatively easily compressible and to impart a spring bias force.

The recess 407 is a cutout portion that provides the tabs 410 with the spring force and which acts as a detent or stop for the raised, leading end 315 of the tabs 310 of the transfer cap 300 (when held within cavity 429). The patient-side connector 400 also defines a second cutout portion 409 that reduces the weight of the overall device and also provides a way of visually inspecting the O-ring 405 held within the O-ring groove 406. Further, the cutout portion 409 provides medical personnel with a way of visually confirming if the transfer cap 300, if held within cavity 429, is properly positioned relative to the O-ring 405 to provide a fluid-tight seal. As mentioned with respect to the day-side connector 200, the patient-side connector 400 includes an optional alignment indicator 404 that provides a visual indicator to the user as to the proper orientation of the patient-side connector 400 relative to the day-side connector (and the respective alignment indicator 204).

Referring to FIGS. 22-25, the transfer cap 300 has a body 301 that includes an annular inlet flange and an annular outlet flange 321 each extending radially outward and circumferentially with respect to the body 301. The tabs 310 are connected to the annular flange 321 and extend axially and circumferentially toward the annular inlet flange 320. The tabs 310 each include leading ends 315 that protrude radially outward from the tabs 310 to snap-fit with the recess 407 in the patient-side connector 400. The annular flange 321 is connected to a pair of alignment members 312 that define axially extending rails 327 along an inner surface thereof. The alignment members 312 are circumferentially offset with respect to the tabs 310 and extend radially outward with respect to axial centerline CL (FIG. 9). The alignment grooves 228a, 228b extend radially inward from an inner surface of the cavity 328 and include a depth sufficient to mate with the height of the corresponding alignment rails 227 of the day-side connector 200, such as with a sliding friction or interference fit. The annular flange 320 acts as a depth stop which operatively abuts against the annular flange 220 of the day-side connector 200 to maintain the transfer cap 300 in a proper axial orientation with respect to the day-side connector 200 and patient-side connector 400.

The annular inlet flange 320 defines an internal cavity 328 having an internal surface that is contoured to mate with and receive the day-side connector 200. The alignment members 312 include a raised, trapezoidally shaped grooves are shaped to correspond to the outer contours of the alignment rails 227 and the inner contours of the raised, trapezoidally shaped grooves 412. The grooves 312 provide a relatively smooth profile to the outer periphery of the transfer cap 300, such as when the transfer cap 300 is connected to the day-side connector 200 and the patient-side connector 400 has been removed, and act as alignment grooves ensuring that the patient-side connector 400 and/or day-side connector 200 are properly positioned and fitted within the cavity 429.

The body 301 includes the annular outlet opening 330 and is reduced in diameter relative to grooves 312, tabs 310 and annular flanges 320, 321. Referring to FIG. 9, the annular outlet opening 330 has a reduced diameter to matingly engage with the O-ring 405 of the annular outlet opening 403 of the patient-side connector 400 to form a fluid tight seal therebetween. In addition, the annular outlet opening 330 operatively abuts against the annular flange 430 of the patient-side connector 400 and is viewable in the window 409 of the patient-side connector.

The quick release tabs 310 are only partially secured along a first edge of the generally rectangular members so that the tabs 310 are relatively easily compressible and to impart a spring bias force to the tabs 310. The recess 307 is a cutout portion that provides the tabs 310 with the spring force and which acts as a detent or stop for the raised, leading end 211 of the tabs 210 of the day-side connector 200 (when held within cavity 328). The recess 317 also acts as an alignment groove for the alignment indicator 204 of the day-side connector 200.

Referring to FIGS. 22-27, the transfer cap 300 includes an annular opening 335 which acts as a valve channel or cylinder for stem 386 of the check valve 380 operatively held therein. The annular opening 335 is sized and shaped to receive the leading end of the male tubing connection 225 of the day-side connector and to form a fluid tight seal with the O-ring 205 and tubing connection 225. In addition, the annular opening 335 and the annular opening 330 are separated by the valve seat 385 which further defines a fluid conduit 388 permitting fluid flow through the transfer cap 300 (if the check valve is opened). The check valve 385 has a valve crown 384 sized and shaped to provide a predetermined surface area that resists fluid flow until a relatively low fluid pressure is achieved, e.g., slightly above atmospheric pressure or other predetermined pressure.

Referring to FIG. 9, the raised leading edge 415 and recesses 407 operatively engage with the adjacent, raised leading edge 315 of the quick release tabs 310 when the transfer cap 300 is properly fitted within an annular opening 428 defined by an upstream side of the patient-side connector 400. The quick release tabs 410, 310 include knurled or profiled surfaces 411, 311 which facilitates the user squeezing the quick release tabs 410, 310 with their fingers. The quick release tabs 410, 310 are relatively rectangular in shape and are secured to the patient-side connector 400 and transfer cap 300 at only a first side, e.g., opposite from the leading edges 415, 315. Therefore, the quick release tabs 410, 310 act as leaf springs that are relatively flexible and are relatively easily compressed by the user squeezing the quick release tabs 410, 310, such as by squeezing tabs 410 to release the patient-side connector 400 from operative engagement with the transfer cap 300. The quick release tabs 310 each include an inherent spring force that biases the tabs 310 into locking position with the surrounding and adjacent patient-side connector.

Referring to FIG. 9, the day-side connector 200, transfer cap 300 and patient-side connector 400 are held together by the cooperative engagement of the raised leading ends 211, 315, 415 of the tabs 310, 410, 310, respectively. For example, when the day-side connector is snap fit within an annular opening 328 defined by the annular flange 320 of the transfer cap 300, the raised, leading ends 211 of the tabs 210 are spring biased to fit within a detent or recess 307 formed within the transfer cap 300. If the transfer cap 300 is secured within the patient-side connector 400 (as shown in FIG. 9), the raised, leading ends 315 of the tabs 310 are spring biased to operatively fit within a detent or recess 407 (see FIG. 16) of the surrounding patient-side connector 400. The recesses (307, 407) are defined by the respective annular flanges 320, 421 of the transfer cap 300 and patient-side connector 400, respectively. The tabs 210, 310, 410 therefore provide a relatively easy way to release and secure the transfer cap 300 and patient-side connector 400 to each other and to the day-side connector 200, such as with a snap, spring-biased fit.

The fluid conduit connector assembly 51 provides a simple, fluid-tight tubing connection between day-side and patient-side tubing sets. In addition, the transfer cap 300, which may be separately left in operative connection with the day-side connector 200, provides a protective covering for the day-side set 35 while patient-side sets are being replaced or between surgeries.

The patient-side set 55 includes the patient side connector 400, the surgical tubing section 50b secured to the annular outlet opening 413, and the transfer cap 300 when a new patient-side set 55 is ready to be attached to the day-side set 35. Typically, the transfer cap 300 is already secured within the interior cavity 429 of the patient side connector 400 when medical personnel secure the patient-side set 55 to the day-side connector 200. However, the transfer cap 300 is also capable of being secured to the day-side connector 200 first, followed by the attachment of the patient-side connector 400 to the transfer cap 300. The pair of alignment grooves 327 mate with and receive corresponding alignment rails 227 which extend axially and circumferentially with respect to centerline CL. The alignment rails 227 and the alignment grooves 327 are sized and shaped to provide a sliding, clearance fit therebetween and to ensure proper positioning of the patient-side set 55 relative to the day-side connector 200. The day-side connector 200, transfer cap 300 and patient-side connector 400 operatively and matingly engage together with a snap-fit and/or interference fit.

The opposing quick release tabs 410 of the patient-side connector 400 permit medical personnel to release the patient-side connector 400 from the snap fit with the underlying transfer cap 300. Medical personnel remove the patient-side connector 400 from the transfer cap 300 by squeezing the quick release tabs 410 and pulling the patient-side connector 400 in a direction away from the day-side connector 200. When the patient-side connector 400 is removed, the transfer cap 300 remains attached to the day-side connector 200, because of the spacing, or gaps 316, between the tabs 410 and the tabs 310. The gaps 316 permit the transfer cap tabs 310 to be depressed sufficiently to release the raised leading ends 315 from the patient-side connector recesses 407 without contacting the day-side connector tabs 210. Thus, as a result of the gaps 316, the patient-side connector 400 can be removed while the transfer cap 300 remains attached to the day-side connector 200.

The transfer cap 300 includes the one-way check valve 380 and protects the male tubing connection 225 of the day-side connector from unnecessary exposure or contamination from debris, air and inadvertent contact while the patient side set 55 is being removed or replaced. The transfer cap 300 also includes quick release tabs 310 permitting medical personnel to release the transfer cap 300 from the snap fit with the underlying day-side connector 200. If medical personnel are ready to connect a new patient-side set 55 to the day-side connector 200, medical personnel remove the transfer cap 300 from the day-side connector 200 by squeezing the quick release tabs 310 on the transfer cap 300 and pulling the transfer cap 300 in a direction away from the day-side connector 200 to expose male tubing connection 225.

Other implementations are within the scope of the following claims. For example, the surgical tubing section 50b can include one or more check valves, such as check valve 52, and/or the check valve 380 can be used instead of check valve 52 to control fluid flow on the patient-side set 55 of system components. In addition, the check valve 380 can be omitted from the fluid conduit connector assembly 51 for use in applications in which there is no requirement to reduce backflow, such as in single-use disposable systems or resterilizable devices. The fluid conduit connector assembly 51 can be applied to tubing, hose, piping and/or any other type of fluid conduit that can be connected in sections.

The fluid conduit connector assembly 51 can be machined or molded from plastic, such as PVC or polypropylene, and/or any other suitable material. One or more of the connectors 200, 300, 400 can be formed partially or entirely from a relatively transparent material, such as clear PVC or polypropylene. In addition, alternative implementations can utilize Luer twist-lock or threaded connections to secure the day-side connector 200 to the transfer cap 300, or to secure the transfer cap 300 to the patient-side connector 400, in lieu of the snap-fit engagement described above. One or both of the connectors 200, 400 can include a face seal 370, 375, instead of the respective O-ring 205, 405, to form a fluid-tight seal against a radial surface of the transfer member 300. Similarly, the transfer member 300 can include one or more face seals 370, 375, in lieu of one or both of the O-rings of the mating connectors 200, 400, to form a fluid-tight seal against a radial surface of the respective mating connector 200, 400. Furthermore, a fluid-tight seal can be formed between one or both of the connectors 200, 400 and the transfer member 300 by a plastic-to-plastic radial interference fit, for example, between the male connector 225 and the annular inlet opening 335, or the annular inlet opening 403 and the annular outlet opening 330.

Referring to FIGS. 28A-28E, an alternative embodiment of a fluid conduit connector assembly 2800 includes a day-side tubing section 50a operatively connected to a patient-side tubing connection 50b through a fluid conduit connector assembly 2800. The device 2800 includes a patient-side connector 2840 having an integral check valve therein (not shown), a protective cap 2830 and a day-side connector 2820. The patient-side connector 2840 threads onto the day-side connector 2820 and seals with a tapered, conical fit. After a surgical procedure is completed, the patient set is removed and the protective cap 2830 is unthreaded from a storage position (FIGS. 28A-28C) and installed on the day-side connector 2820. The patient-side tubing 50b and patient-side connector 2840 can be discarded and the protective cap 2830 remains in place until the next patient-side set is ready to be connected.

Referring to FIGS. 29A-29D, an alternative embodiment of a fluid conduit connector assembly 2900 includes a day-side tubing section 50a operatively connected to a patient-side tubing connection 50b through a fluid conduit connector assembly 2900. The device 2900 includes a patient side connector 2940, a day-side connector 2920, a protective cap 2930 integrally formed and connected to the day-side connector 2920, and a pinch clamp valve 2925 for controlling fluid flow in the day-side tubing section 50a. The patient-side connector 2940 is threaded or twisted onto the day-side connector 2920, such as with a typical threaded or twist-lock Luer connection or other tapered, conical fit. The surgical procedure is performed, the surgical tubing section 50a is clamped with clamp 2925 and the patient-side connector 2940 is removed. The protective cap 2930 is secured over the exposed end of the day-side connector 2920 and the day-side set 35 is protected until the next patient-side connector 2940 is ready to be connected. The patient-side connector 2940 can also include a check valve assembly to maintain fluid flow in a single direction, e.g., from the day-side to the patient-side only.

Figure 34:
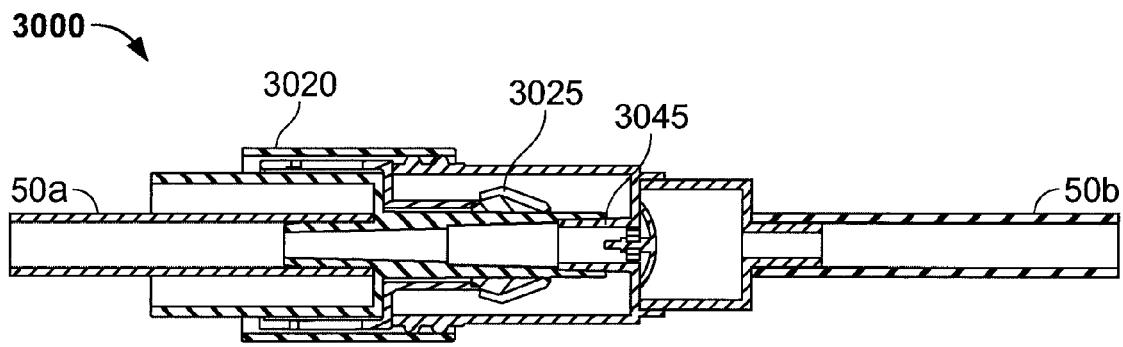
FIG. 34 is a sectional view of the fluid conduit connector assembly taken along line 33-33 and with a male luer connector operatively connected with a female luer connector.
Figure 35:
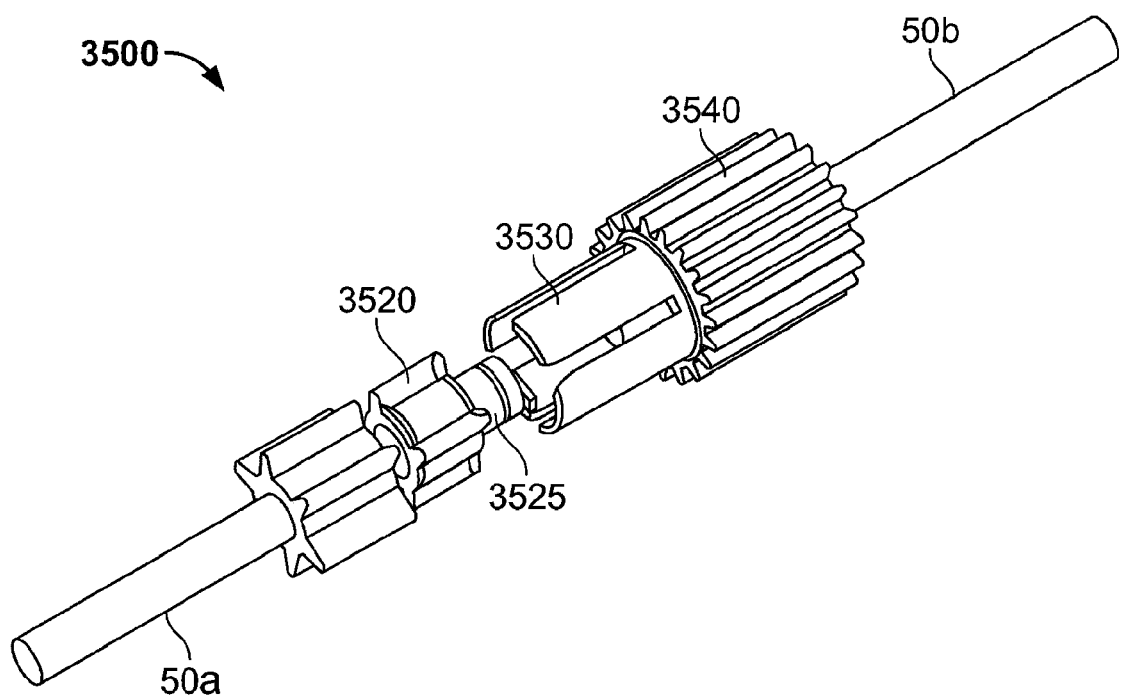
FIG. 35 is a perspective view of a fluid conduit connector assembly according to a another embodiment.
Figure 36:
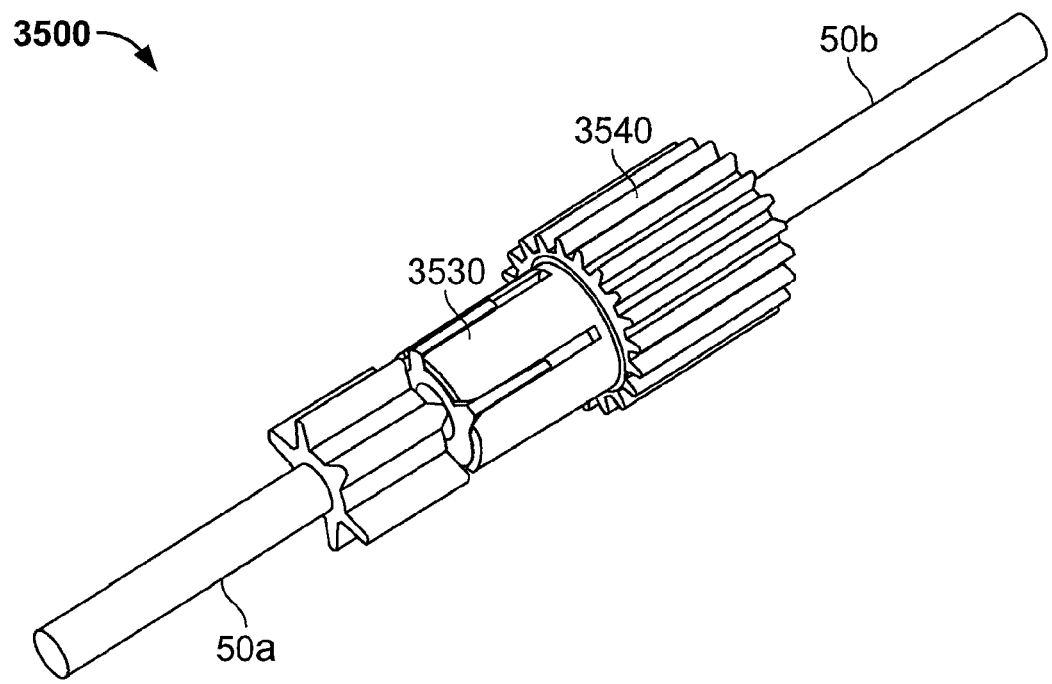
FIG. 36 is a perspective view of the fluid conduit connector assembly of FIG. 35 showing a patient-side tubing connector operatively connected to a day-side tubing connector.
Figure 37:
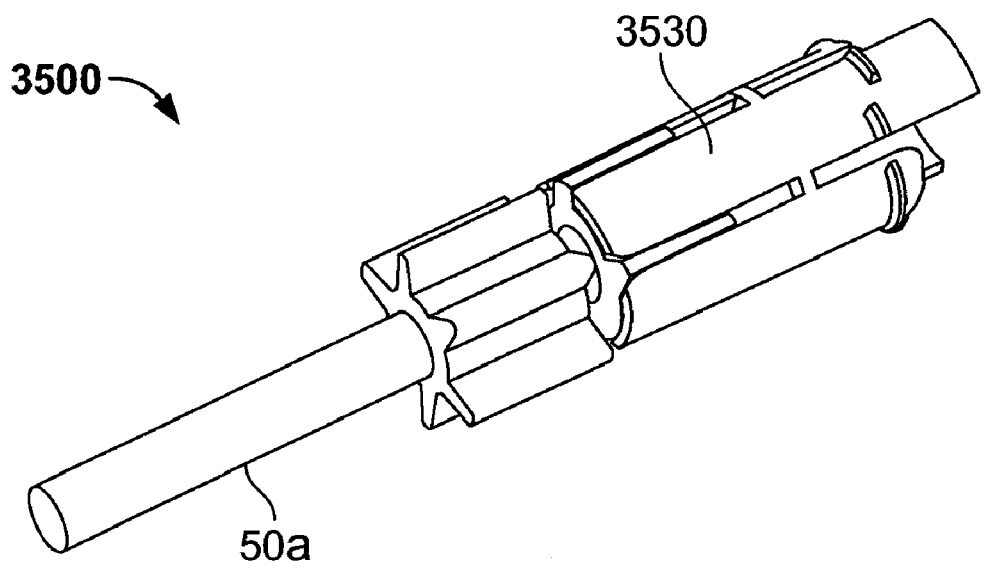
FIG. 37 is a perspective view of the fluid conduit connector assembly of FIG. 35 with a patient-side tubing connector removed.
Figure 38:
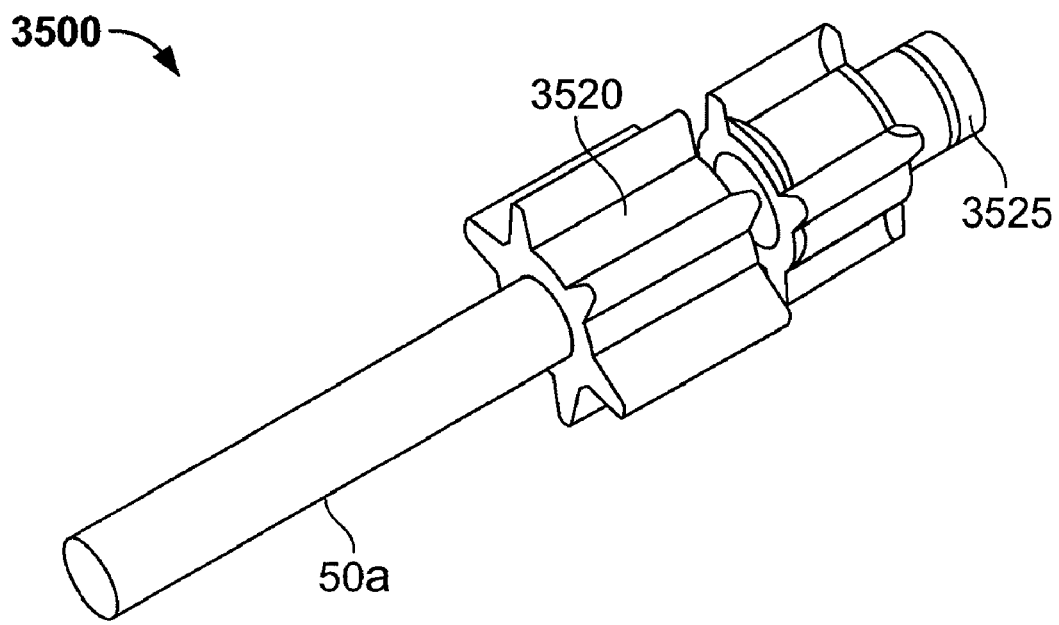
FIG. 38 is a perspective view of the fluid conduit connector assembly of FIG. 35 with transfer cap removed.

Referring to FIGS. 30-34, an alternative embodiment of a fluid conduit connector assembly 3000 includes a day-side tubing section 50a operatively connected to a patient-side tubing connection 50b through a fluid conduit connector assembly 3000. The device 3000 includes a patient-side connector 3040 having an integrated check valve 3080, and a day-side connector 3020. The patient-side connector 3040 includes a protective shield 3045 and a male tubing connection 3045. The day-side connector 3020 includes a flexible shroud 3025 that is compressible between a protective, conical profile (FIG. 33), and a compressed, open state (FIG. 34). The flexible shroud 3025 encapsulates the sealing surfaces of the day-side connector and maintains cleanliness by avoiding direct contact with any contaminated surfaces. The patient-side connector 3040 is threaded together with the day-side connector 3020. The patient-side connector 3040 is rotated until the shroud 3025 compresses to expose a fluid flow path within the day-side connector 3020 to a fluid flow conduit 3045 of the patient-side connector 3040. Although no transfer cap is provided, the patient-side connector 3040 and protective shroud 3020 protect the day-side set 35 from contamination by avoiding unnecessary exposure of the fluid flow path of the day-side connector 3020 unless the shroud is compressed and connected to the patient-side connector 3040 (FIG. 34).

Referring to FIGS. 35-40, an alternative embodiment of a fluid conduit connector assembly 3500 includes a day-side tubing section 50a operatively connected to a patient-side tubing connection 50b through a fluid conduit connector assembly 3500. The device includes a day-side connector 3520, a transfer cap 3530, and a patient-side connector 3540. The patient-side connector 3540 includes an umbrella valve or check valve 3580. The patient side connector 3540 is snap-fit onto the day connector 3520. The patient-side connector 3540 includes the integral transfer cap 3530 which includes bayonet-type mount for engaging a corresponding surface of the day-side connector 3520 and male fluid outlet 3525. The transfer cap 3530 is not removed until the patient-side connector 3540 is removed. The patient-side connector 3540 is removed by unscrewing the connector 3540 from the transfer cap 3530. The downstream end of the transfer cap 3530 includes a releasing tab that is then squeezed to release the transfer cap 3530 from the day-side connector (FIG. 38) when the next patient-side set is ready for use.

A number of embodiments have been described. Nevertheless, it will be understood that various modifications may be made. For example, any of the aforementioned embodiments can incorporate a snap-fit, a twist-lock or threaded engagement between the day-connector, transfer cap, protective cap, and/or patient-side connector. The aforementioned devices can incorporate one or more check valves or other valves, such as a high flow, duckbill, umbrella or ball check valve. Any of the aforementioned devices can be used in conjunction with tubing clamps that facilitate isolating fluid flow within surgical tubing connections as patient-side sets 55 are operatively connected and disconnected from day-side sets 35. Although the transfer cap of some of the above embodiments has been described as a separate member, the transfer cap could be eliminated and the check valve incorporated into the patient side connector. In such an embodiment, when the patient side connector is removed from the day set, the user would cover the day set connector with an aseptic covering.

Accordingly, other embodiments are within the scope of the following claims.

What is claimed is:

1. A fluid conduit connector assembly, comprising:
   a transfer member having a fully circumferentially enclosed body with an inner surface defining a fluid channel, and including an inlet region for flow of fluid into the fluid channel, and an outlet region for flow of fluid from the fluid channel, the transfer member further including:
   a rigid axial alignment member attached to the body and arranged outward of the body; and
   a pair of flexible tabs arranged generally circumferentially of the alignment member and outward of the body such that the flexible tabs are movable relative to the body from a rest position toward an insert position and back toward the rest position; a day-side connector; and a patient-side connector,
   wherein, when the day-side connector is coupled to the transfer member, the pair of flexible tabs are configured to align with a pair of flexible tabs of the day-side connector, such that the day-side connector is capable of being fully spaced apart from the transfer member as a result of the interaction between the pair of flexible tabs of the transfer member and the flexible tabs of the day-side connector and a force applied in a direction that separates the transfer member from the day-side connector, and
   wherein the pair of flexible tabs are configured to align with a pair of flexible tabs on the patient-side connector and couple the transfer member to the patient-side connector when the transfer member is coupled to the patient-side connector, such that the transfer member is capable of being fully spaced apart from the patient-side connector as a result of the interaction between the pair of flexible tabs of the patient-side connector and the flexible tabs of the transfer member and a force applied in a direction that separates the patient-side connector from the transfer member.

2. The fluid conduit connector assembly of claim 1, further comprising an annular flange connecting the alignment member and the tabs.

3. The fluid conduit connector assembly of claim 1, further comprising an opposing axial alignment member outward of the body.

4. The fluid conduit connector assembly of claim 1, wherein the outlet region of the day-side connector has an outer surface defining an annular groove.

5. The fluid conduit connector assembly of claim 4, further comprising an O-ring within the annular groove of the day-side connector.

6. The fluid conduit connector assembly of claim 1, wherein the outlet region of the body includes a face seal.

7. The fluid conduit connector assembly of claim 1, wherein the inlet region of the patient-side connector has an outer surface defining an annular groove.

8. The fluid conduit connector assembly of claim 7, further comprising an O-ring within the annular groove of the patient-side connector.

9. The fluid conduit connector assembly of claim 1, wherein the inlet region of the body includes a face seal.

10. The fluid conduit connector assembly of claim 1 wherein the transfer member includes a check valve.

11. The fluid conduit connector assembly of claim 1 wherein the transfer member includes an opposing axial alignment member outward of the body.

12. The fluid conduit connector assembly of claim 11 wherein the transfer member alignment members face inward and the transfer member further comprises an opposing pair of alignment members facing outward.

13. The fluid conduit connector assembly of claim 1, wherein the day-side connector includes a body with an inner surface defining a fluid channel, and including an inlet region for flow of fluid into the fluid channel, and an outlet region for flow of fluid from the fluid channel, the day-side connector further including:
   an axial alignment member outward of the body; and
   a pair of flexible tabs arranged generally circumferentially of the alignment member and outward of the body.

14. The fluid conduit connector assembly of claim 13, wherein the day-side connector includes a body with an inner surface defining a fluid channel, and includes an inlet region for flow of fluid into the fluid channel, and an outlet region for flow of fluid from the fluid channel, the day-side connector further including:
   an axial alignment member outward of the body; and
   a pair of flexible tabs arranged generally circumferentially of the alignment member and outward of the body,
   wherein each of the alignment members and each of the tabs are aligned such that the day-side connector, the patient-side connector, and the transfer member can be attached by sliding the alignment members relative to each other, and detached by pressing on respective tabs.

15. A fluid conduit connector assembly, comprising:
   a day-side connector including a body and a pair of flexible tabs that are movable relative to the day-side connector body from a rest position toward an insert position and back toward the rest position;
   a patient-side connector including a body and a pair of flexible tabs that are movable relative to the patient-side connector body from a rest position toward an insert position and back toward the rest position; and
   a transfer member including a body and a pair of flexible tabs that are movable relative to the transfer member body from a rest position toward an insert position and back toward the rest position, the three pairs of tabs configured such that the transfer member releasably couples the day-side and patient-side connectors,
   wherein, when the transfer member releasably couples the day-side and patient-side connectors:
      the pair of flexible tabs of the day-side connector couple the day-side connector to the transfer member,
      the pair of flexible tabs of the transfer member couple the transfer member to the patient-side connector,
      the pair of flexible tabs of the transfer member are configured to interact with the flexible tabs of the day-side connector to release the day-side connector from the transfer member, such that the day-side connector is capable of being fully spaced apart from the transfer member as a result of the interaction between the pair of flexible tabs of the transfer member and the flexible tabs of the day-side connector and a force applied in a direction that separates the transfer member from the day-side connector, and
      the pair of flexible tabs of the patient-side connector are configured to interact with the flexible tabs of the transfer member to release the transfer member from the patient-side connector, such that the transfer member is capable of being fully spaced apart from the patient-side connector as a result of the interaction between the pair of flexible tabs of the patient-side connector and the flexible tabs of the transfer member and a force applied in a direction that separates the patient-side connector from the transfer member.

16. The fluid conduit connector assembly of claim 15 wherein the day-side connector, the patient-side connector, and the transfer member each include an alignment member such that when coupled, the alignment members cause the three pairs of tabs to align.

17. The fluid conduit connector assembly of claim 15 wherein, when the transfer member couples the day-side and patient-side connectors, the three pairs of flexible tabs overlap.

18. The fluid conduit connector assembly of claim 15, wherein the transfer member further comprises a pair of recesses that each define one of the pair of flexible tabs of the transfer member, and wherein the pair of flexible tabs of the day-side connector fit into the pair of recesses of the transfer member to couple the day-side connector to the transfer member.

19. The fluid conduit connector assembly of claim 15, wherein the patient-side connector further comprises a pair of recesses that each define one of the pair of flexible tabs of the patient-side connector, and wherein the pair of flexible tabs of the transfer member fit into the pair of recesses of the patient-side connector to couple the transfer member to the patient-side connector.

20. The fluid conduit connector assembly of claim 15, wherein the pair of flexible tabs of the patient-side connector are configured to interact with the flexible tabs of the transfer member to release the transfer member from the patient-side connector, such that the transfer member is capable of being fully spaced apart from the patient-side connector as a result of the interaction between the pair of flexible tabs of the patient-side connector and the flexible tabs of the transfer member and a force applied in a direction that separates the patient-side connector from the transfer member while the transfer member remains coupled to the patient-side connector.

21. The fluid conduit connector assembly of claim 15, wherein the force applied in the direction that separates the patient-side connector from the transfer member is a pulling force.

22. A fluid conduit connector assembly, comprising:
a day-side connector including a pair of flexible tabs;
a patient-side connector including a pair of flexible tabs; and
a transfer member including a pair of flexible tabs, the three pairs of tabs configured such that the transfer member releasably couples the day-side and patient-side connectors,
wherein, when the transfer member couples the day-side and patient-side connectors:
the three pairs of flexible tabs radially overlap,
the pair of flexible tabs of the day-side connector couple the day-side connector to the transfer member,
the pair of flexible tabs of the transfer member couple the transfer member to the patient-side connector,
the pair of flexible tabs of the transfer member are configured to interact with the flexible tabs of the day-side connector to release the day-side connector from the transfer member, such that the day-side connector is capable of being fully spaced apart from the transfer member as a result of the interaction between the pair of flexible tabs of the transfer member and the flexible tabs of the day-side connector and a force applied in a direction that separates the transfer member from the day-side connector, and
the pair of flexible tabs of the patient-side connector are configured to interact with the flexible tabs of the transfer member to release the transfer member from the patient-side connector, such that the transfer member is capable of being fully spaced apart from the patient-side connector as a result of the interaction between the pair of flexible tabs of the patient-side connector and the flexible tabs of the transfer member and
a force applied in a direction that separates the patient-side connector from the transfer member.

23. The fluid conduit connector assembly of claim 22, wherein the day-side connector, the patient-side connector, and the transfer member each include an alignment member such that when coupled, the alignment members cause the three pairs of tabs to align.

24. A fluid conduit connector assembly, comprising:
a day-side connector including a pair of flexible tabs;
a patient-side connector including a pair of flexible tabs; and
a transfer member including a body having a longitudinal axis and a pair of flexible tabs, the three pairs of tabs configured such that the transfer member releasably couples the day-side and patient-side connectors,
wherein, when the transfer member couples the day-side and patient-side connectors:
a plane transverse to the longitudinal axis of the transfer member body passes through the three pairs of flexible tabs,
the pair of flexible tabs of the day-side connector couple the day-side connector to the transfer member,
the pair of flexible tabs of the transfer member couple the transfer member to the patient-side connector,
the pair of flexible tabs of the transfer member are configured to interact with the flexible tabs of the day-side connector to release the day-side connector from the transfer member, such that the day-side connector is capable of being fully spaced apart from the transfer member as a result of the interaction between the pair of flexible tabs of the transfer member and the flexible tabs of the day-side connector and a force applied in a direction that separates the transfer member from the day-side connector, and
the pair of flexible tabs of the patient-side connector are configured to interact with the flexible tabs of the transfer member to release the transfer member from the patient-side connector, such that the transfer member is capable of being fully spaced apart from the patient-side connector as a result of the interaction between the pair of flexible tabs of the patient-side connector and the flexible tabs of the transfer member and a force applied in a direction that separates the patient-side connector from the transfer member.

25. The fluid conduit connector assembly of claim 15, wherein the day-side connector, the patient-side connector, and the transfer member each include an alignment member such that when coupled, the alignment members cause the three pairs of tabs to align.

* * * * *